(12) United States Patent
Culligan et al.

(10) Patent No.: US 8,418,851 B2
(45) Date of Patent: Apr. 16, 2013

(54) APPARATUS FOR HOUSING A PLURALITY OF NEEDLES AND METHOD OF USE THEREFOR

(76) Inventors: Patrick John Culligan, Madison, NJ (US); Roger P. Goldberg, Evanston, IL (US); Douglas S. Scherr, Scarsdale, NY (US)

( * ) Notice: Subject to any disclaimer, the term of this patent is extended or adjusted under 35 U.S.C. 154(b) by 0 days.

(21) Appl. No.: 13/358,864

(22) Filed: Jan. 26, 2012

(65) Prior Publication Data

US 2012/0123472 A1    May 17, 2012

Related U.S. Application Data

(63) Continuation-in-part of application No. 12/858,107, filed on Aug. 17, 2010.

(60) Provisional application No. 61/334,036, filed on May 12, 2010, provisional application No. 61/234,537, filed on Aug. 17, 2009.

(51) Int. Cl.
*A61B 17/06* (2006.01)

(52) U.S. Cl.
USPC .......................................... 206/380; 606/222

(58) Field of Classification Search .................. 206/380; 606/222–233
See application file for complete search history.

(56) References Cited

U.S. PATENT DOCUMENTS

| | | | |
|---|---|---|---|
| 2,831,572 A | 4/1958 | Anthony | |
| 3,227,265 A | 1/1966 | Joseph | |
| 3,944,069 A | 3/1976 | Eldridge | |
| 4,120,397 A * | 10/1978 | Neumann | 206/370 |
| 4,243,140 A | 1/1981 | Thrun | |
| 4,254,862 A | 3/1981 | Barratt | |
| 4,418,821 A | 12/1983 | Sandel | |
| 4,596,329 A | 6/1986 | Eldridge | |
| 4,637,513 A | 1/1987 | Eldrige | |
| 4,736,844 A * | 4/1988 | Scott et al. | 206/370 |
| 4,967,902 A | 11/1990 | Sobel | |
| 5,024,323 A | 6/1991 | Bolton | |
| 5,145,063 A * | 9/1992 | Lee | 206/364 |
| 5,344,005 A | 9/1994 | Kettner | |
| 5,350,060 A | 9/1994 | Alpern et al. | |
| 5,538,132 A | 7/1996 | Propp et al. | |
| 5,617,952 A | 4/1997 | Kranendonk | |
| 5,799,788 A | 9/1998 | Webb | |
| 5,887,706 A | 3/1999 | Pohle et al. | |
| 6,659,270 B2 | 12/2003 | Williamson et al. | |
| 6,719,128 B2 | 4/2004 | Alpern et al. | |

(Continued)

OTHER PUBLICATIONS

Written Opinion of the International Searching Authority for PCT/US10/45762; pp. 1-5; Oct. 6, 2010.

*Primary Examiner* — J. Gregory Pickett
*Assistant Examiner* — Ernesto Grano
(74) *Attorney, Agent, or Firm* — Sean M. Kavanaugh Esq.

(57) ABSTRACT

An apparatus houses a plurality of surgical elements, such as needles and sutures, both before and after use. The largest cross-sectional dimension of the housing is preferably less than about 12 mm. In some embodiments, the apparatus includes a substantially rigid housing having a first section that holds a plurality of unused needles and a second section that receives the plurality of needles after use. In other embodiments, the apparatus includes a flexible panel having a plurality of pockets therein, wherein each pocket is configured to house a single needle.

20 Claims, 30 Drawing Sheets

U.S. PATENT DOCUMENTS

| | | |
|---|---|---|
| 6,986,780 B2 * | 1/2006 | Rudnick et al. ............... 606/222 |
| 7,036,661 B2 | 5/2006 | Anthony et al. |
| 7,070,051 B2 * | 7/2006 | Kanner et al. ................ 206/382 |
| 7,353,946 B2 | 4/2008 | Cervantes |
| 7,441,660 B2 | 10/2008 | Caron |
| 7,497,330 B2 | 3/2009 | Anthony et al. |
| 2003/0155259 A1 | 8/2003 | Koseki |
| 2004/0050721 A1 | 3/2004 | Roby et al. |
| 2004/0129591 A1 | 7/2004 | Koseki |
| 2005/0269228 A1 | 12/2005 | Kanner et al. |
| 2007/0055294 A1 | 3/2007 | Giap |
| 2008/0243141 A1 | 10/2008 | Privitera et al. |

* cited by examiner

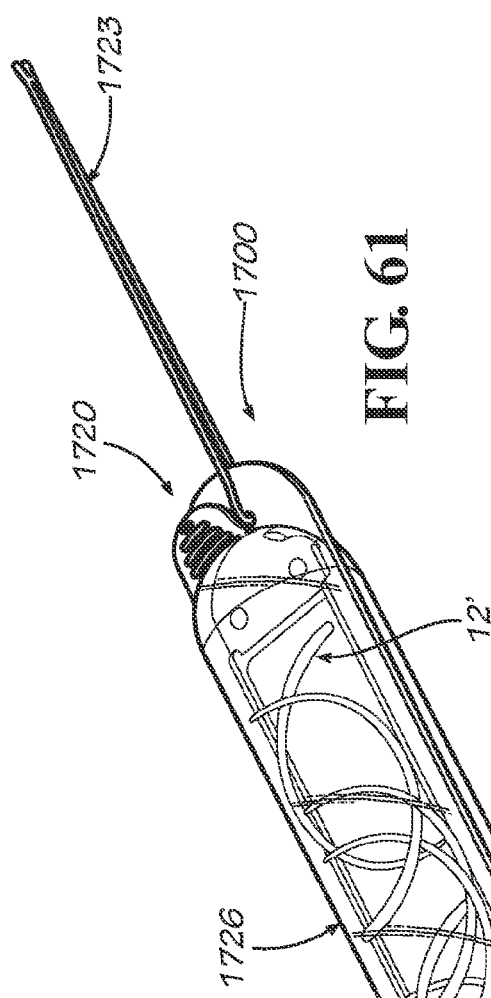
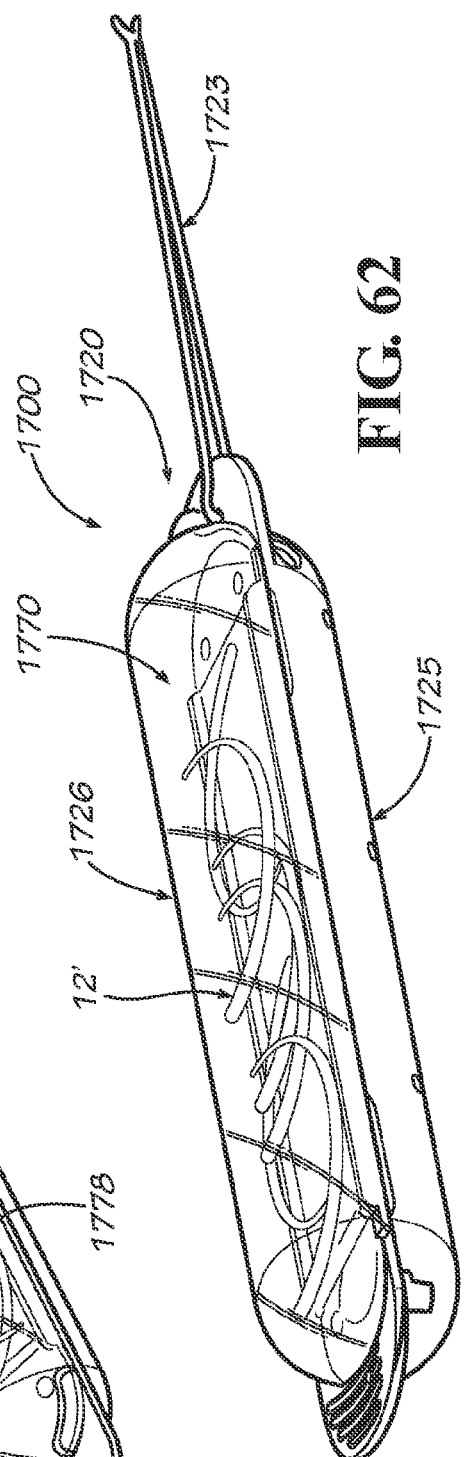
FIG. 61
FIG. 62

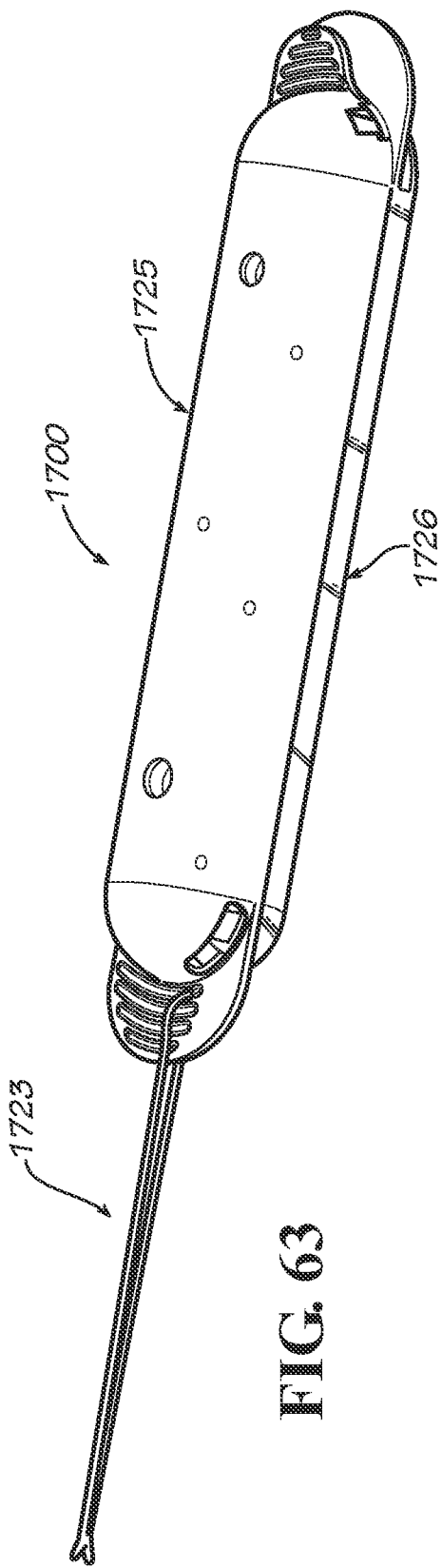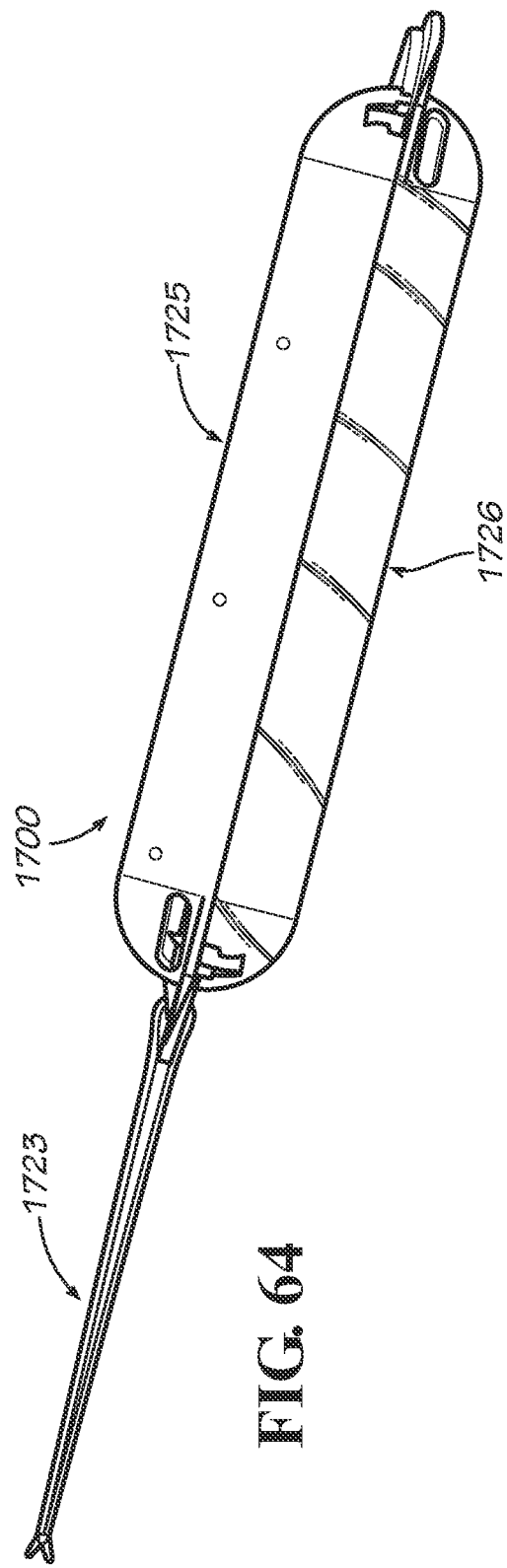
FIG. 63
FIG. 64

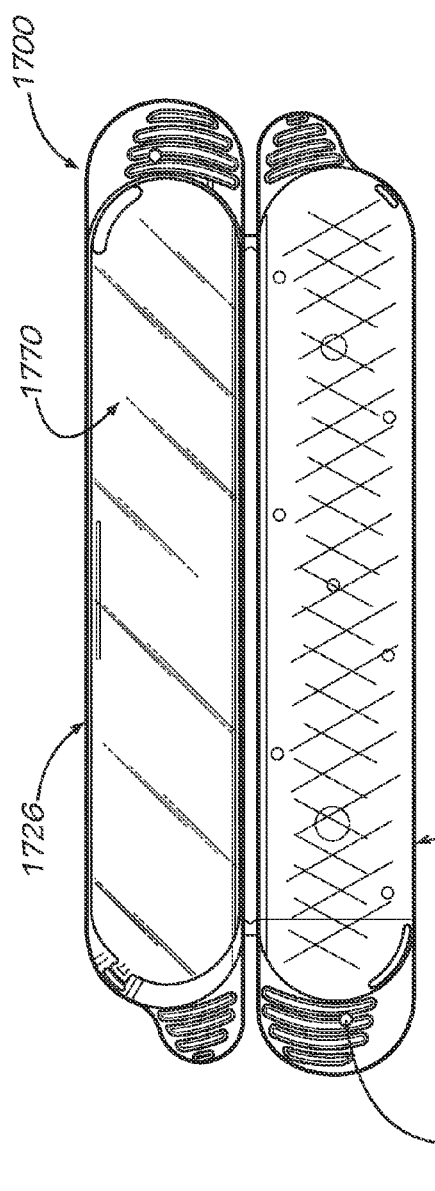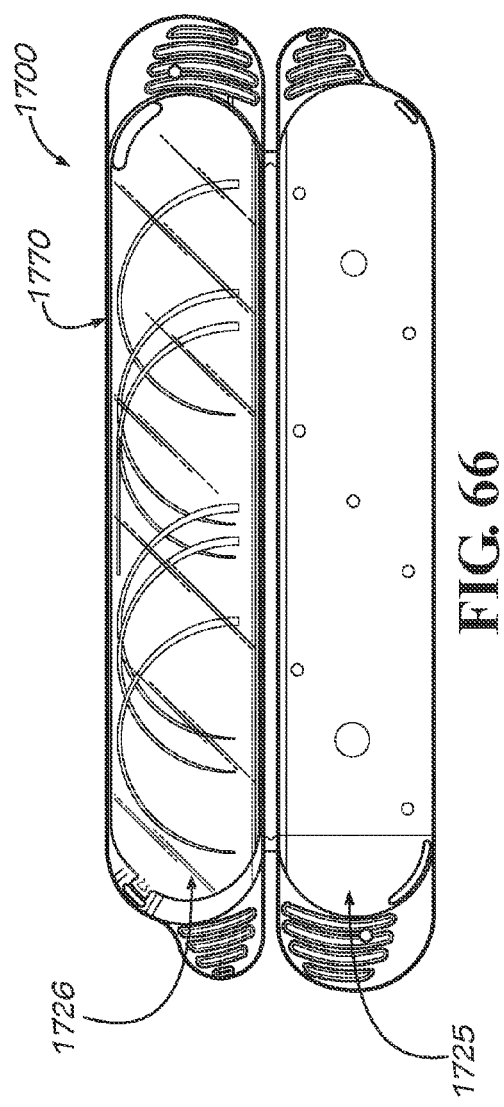

APPARATUS FOR HOUSING A PLURALITY OF NEEDLES AND METHOD OF USE THEREFOR

CROSS REFERENCE TO RELATED APPLICATIONS

This application is a continuation-in-part of U.S. patent application Ser. No. 12/858,107, filed Aug. 17, 2010, which claims priority to U.S. Provisional Patent Application Ser. Nos. 61/234,537, filed Aug. 17, 2009 and 61/334,036, filed May 12, 2010, all of which are hereby incorporated herein by reference in their entireties for all purposes.

FIELD OF THE INVENTION

The present invention relates generally to the field of medical devices, and in particular to an apparatus for housing a plurality of surgical suturing needles and a method of use therefor in robot-assisted endoscopic surgery.

BACKGROUND

Many laparoscopic surgeries are performed using robotic technology, such as the DA VINCI® surgical system. One such procedure that can be performed with the use of the DA VINCI® surgical system is a sacrocolpopexy, which is a surgical procedure to correct vaginal vault prolapse. During this procedure, the surgeon positions mesh to support the vagina. In so doing, a surgeon does a lot of suturing. It is not uncommon for a surgeon to use 16-24 separate sutures in a single procedure. The process of suturing is quite time-consuming and requires a very skilled assistant to pass the needles, each carrying a suture, to the surgeon controlling the robotic arm. Also typically, such needles are passed to the surgeon within the patient's abdomen. Thus, the assistant must be skilled and highly trained so as to avoid nicking an artery or other tissue while passing the needles.

SUMMARY

The present invention provides an apparatus for housing a plurality of surgical elements, such as needles, each threaded with a suture, for use in robot-assisted endoscopic surgery. In a first form, the apparatus has a housing, wherein the housing has a largest cross-sectional dimension of less than about 12 mm so that it's sized and shaped for fitting through a trocar and being temporarily emplaced into a subject's body. The housing further has a first section that holds a plurality of unused needles, wherein each unused needle is threaded with a suture, and a second section that is distinct from the first section, wherein the second section receives the plurality of needles after use.

In another form, the apparatus includes a flexible panel having a plurality of pockets therein. Each pocket can be configured to house a single needle. The panel can be configured to roll up into a generally cylindrical structure having a diameter of no more than about 12 mm. Optionally, a disposal chamber can be attached to a base portion of the panel. Accordingly, the panel can be configured to wrap around the disposal chamber in its closed configuration.

In still another form, the apparatus includes a housing, a foldable panel housed within the housing and attached to at least a portion of the housing, and disposal means within the housing for receiving the plurality of needles after use. The foldable panel includes a plurality of segments, wherein each segment securely holds a single unused needle.

In yet another form, the housing of the apparatus includes at least one outer wall (or portion thereof) that is substantially transparent or semi-transparent such that the needles in the housing can be seen and counted before removing the apparatus from the subject's body. And in yet still another form, the apparatus includes at least one pull cord coupled to an end of the housing such that the cord can be pulled to easily remove the apparatus from the subject's body through the trocar.

The present invention further provides methods for using the apparatus of the present invention in robot-assisted endoscopic surgery. The methods include the steps of placing the apparatus inside a human or animal subject; opening the apparatus to reveal the plurality of needles; removing a first needle from the apparatus; using the first needle to suture tissue; storing the first needle in the housing; repeating for as many additional needles as desired; closing the apparatus; and removing the apparatus from the subject.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIGS. 61-62 are top perspective views of an apparatus for housing a plurality of needles according to another example embodiment, shown in a closed configuration with used needles in the enclosed chamber.

FIGS. 63-64 are bottom perspective views of the apparatus FIGS. 61-62 shown in a closed configuration with no used needles in the enclosed chamber.

FIG. 65 is a top view of the apparatus of FIGS. 61-62, shown in an opened configuration to reveal the inner surfaces and shown without the first needle holder, the internal divider wall and door, or the tab cord.

FIG. 66 is a bottom view of the apparatus of FIG. 65 showing the outer surfaces.

DETAILED DESCRIPTION OF EXAMPLE EMBODIMENTS

Figure 1A:
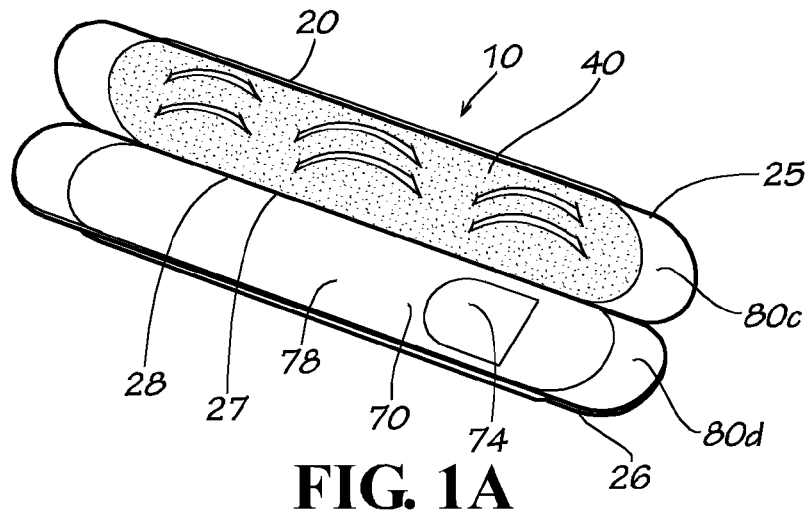
FIG. 1A is a perspective view of an apparatus for housing a plurality of needles according to an example embodiment of the present invention and shown in an open configuration.

The present invention may be understood more readily by reference to the following detailed description of the invention taken in connection with the accompanying drawing figures, which form part of this disclosure. It is also understood that this invention is not limited to the specific devices, methods and conditions or parameters described and/or shown herein, and that the terminology used herein is for the purpose of describing particular embodiments by way of example only and is not intended to be limiting of the claimed invention. Also, as used in the specification including the appended claims, the singular forms "a", "an" and "the" include the plural, and reference to a particular numerical value indicates at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about", it will be understood that the particular value forms another embodiment.

The present invention provides canisters or apparatuses for housing a plurality of surgical elements, such as needles with associated/threaded sutures. Such canisters can be used with robotic surgical technology, such as with the DA VINCI® surgical system, and can be placed and manipulated inside the body of a human or animal subject. The canisters of the present invention can also be used in standard laparoscopic surgery such as when a practitioner (e.g., a surgeon) performs an intra-corporeal knot tying technique or other technique for "auto-fixation" of suture material. The present invention can be used in any robotic-assisted endoscopic surgical procedure that requires the placement of multiple sutures, including gynecologic surgery, urogynecologic surgery, urologic surgery, thoracic surgery, general surgery, any other such surgical procedure done in the abdomen, pelvis, or thoracic cavity.

Preferably, each apparatus holds a plurality of new, sterile needles, and after they are used, also contains the used needles in a disposal portion of the device. In other words, the apparatus can also serve as a needle disposal device. Advantageously, the disposal portions of the apparatuses provide safe storage areas for the used needles and allow the practitioner to safely remove the used needles from the human or animal subject (without risk of nicking an artery or other tissue). Additionally, by containing the used needles with the disposal portions, operating staff and nurses can easily check and account for all used needles after the apparatus has been removed from the human or animal subject.

In one commercial embodiment, the apparatus can have a generally cylindrical, substantially-rigid plastic housing that is approximately 5 cm long and 11 mm in diameter. Preferably, the housing has a diameter or largest cross-sectional dimension that is less than about 12 mm, which allows the housing to be inserted into a typical surgical incision or portion for laparoscopic surgery. Although the housings of many of the example embodiments are shown as generally cylindrical, any suitably shaped housing can be employed and be within the scope of the present invention, including polygonal-shaped, box-shaped, and generally semi-cylindrically shaped. Additionally, the dimensions of the housing can vary as desired (and hence the apparatus can be larger or smaller) and still be within the scope of the present invention. Moreover, any biocompatible material can be used to construct the housing, including hard plastics and metals such as stainless steel. Alternatively, a flexible or substantially non-rigid material can be used for the housing.

The example embodiments depicted herein show various apparatuses that each hold six needles with associated sutures, although the apparatuses of the present invention can be made to accommodate any suitable number and types of needles and associated sutures or other surgical elements. Additionally, a single apparatus can house different sizes and types of needles and sutures or other surgical elements.

Figure 2:
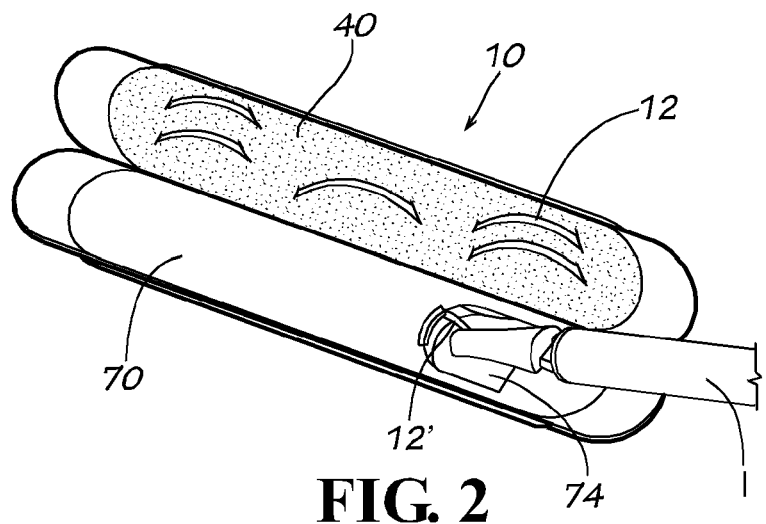
FIG. 2 is a perspective view of the apparatus of FIG. 1A and showing a used needle being placed inside a disposal portion of the apparatus.

In a first example embodiment as depicted in FIGS. 1-2, an apparatus 10 houses six needles 12, each with an associated suture 14 (and for ease of illustration, only one suture 14 is shown). In this embodiment, the needles 12 depicted are generally curved surgical needles (such as "SH needles" manufactured by Ethicon, Inc. or "TH-26 needles" manufactured by W.L. Gore & Associates, Inc.). And the sutures can be of a conventional type, including barbed sutures such as V-LOC sutures by Covidien (North Haven, Conn.) or QUILL sutures by Angiotech Pharmaceuticals, Inc. (Vancouver, Canada). However, any other suitable types, sizes, and number of conventional or custom-designed needles and sutures can be used.

The apparatus 10 includes a housing manipulable between a closed position (in which the needles 12 are enclosed within the internal space of the closed housing) and an open position (in which the unused needles accessible for removal for suturing use). In typical embodiments, the apparatus 10 has an elongated and generally cylindrical housing 20 or body that has a hinge 28 along a longitudinal edge 27 thereof. Preferably, the housing 20 is a substantially rigid, clamshell-type housing such that once opened, the housing comprises two halves or sections 25 and 26. In other embodiments, the two sections are not equal in size and shape. In one alternative embodiment, the housing can be in the form of two cylinders with open ends that couple together to form a substantially enclosed housing, with one cylinder defining the first section holding the unused needles and the other cylinder defining the second holding the used needles. In other embodiments, the housing has a base and a longitudinally sliding cover, with the first and second sections (holding the unused and used needles, respectively) positioned side-by-side in the base.

The first section 25 includes a first needle and suture holder 40. In the depicted embodiment, the needle and suture holder 40 is a piece of a foam material into which the needles 12 with associated sutures 14 are "tacked." In other words, both ends of the needles 12 can be placed into the foam material and securely held therein. Preferably, the foam material is a rigid foam material, although other foam material, such as a soft foam material, can be employed. However, other suitable tackable materials, such as but not limited to silicone or other polymer, can be employed as well. The holder 40 securely holds the plurality of sterile needles 12 and associated sutures 14 within the apparatus 10. In other embodiments, the needles 12 are provided without the sutures 14 pre-threaded onto them.

Figure 1B:
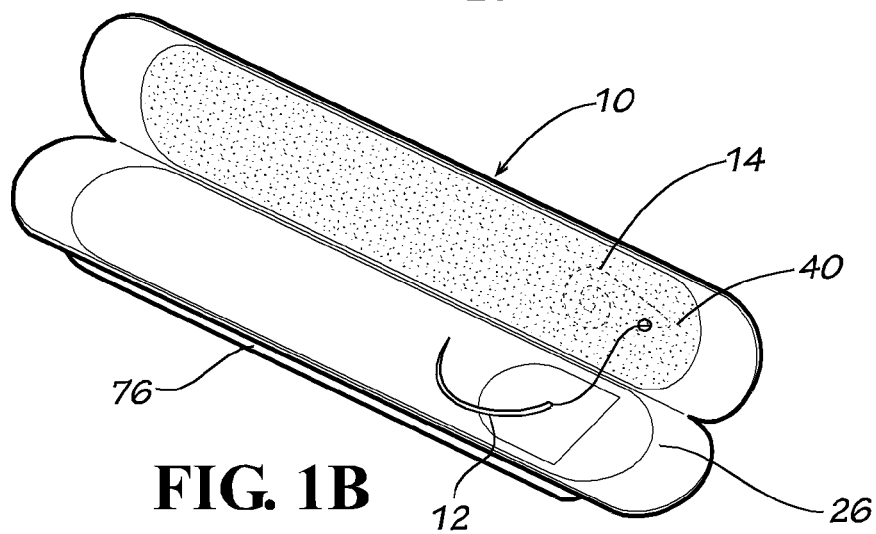
FIG. 1B is a perspective view of the apparatus of FIG. 1A and showing a single needle (for purposes of clarity) with its associated suture housed behind a foam member thereof.

The first needle holder 40 can be provided by a sheet or slab of tackable material having a uniform thickness. In this way, the sutures 14 can be stored in the cavity between the holder 40 and the generally semi-cylindrical wall of the first section 25 of the housing 20, as shown in FIG. 1B. As shown, the sutures 14 (and only one of which is shown for ease of illustration) are inserted through the foam bed/needle holder 40 and held between the foam bed and rear wall of the first section 25 of the housing 20. Optionally, the sutures can be trained around posts and/or onto an adhesive layer. The holder 40 can be fixedly attached in place to the housing 20 (e.g., by a friction fit, mating tabs and slots, or adhesive), it can be hingedly attached to the housing (such as for ease of removing the needles 12 and the associated sutures 14), or it can be completely removable from the housing. Alternatively, the holder 40 can be provided by a generally semi-cylindrical piece of material that generally conforms to the shape of the generally semi-cylindrical wall of the first section 25 of the housing 20, with the sutures 14 compressed between the holder and the housing.

Also preferably, the needles 12 are arranged in the needle holder 40 so that they can be easily grasped by an instrument I of the robotic surgical system (such as an ENDOWRIST® instrument of the DA VINCI® surgical system) or other suitable instruments, such as conventional laparoscopic graspers or needle drivers. As shown, the needles are generally aligned in two rows with three needles in each row. However, the needles can be arranged in any suitable arrangement.

The second section 26 of the housing 20 preferably includes a second needle holder such as a substantially enclosed disposal chamber 70 with a door 74 (e.g., a panel, one-way valve, or hatch) that provides access thereto. In other words, the generally semi-cylindrical wall 76 of the second section of the housing and an upper divider wall 78 cooperatively define the generally enclosed chamber 70. The upper wall 78 can be constructed of the same material as the housing, or any suitable material can be used. As shown, the door 74 has a generally semi-circular shape with a hinge along the straight edge thereof, although any suitably sized and shaped door can be used. Preferably, the door 74 is a pressure-sensitive flap that can be depressed to access the chamber 70, as shown more clearly in FIG. 2. In other words, the door 74 can be spring-biased (e.g., using a torsional spring, a leaf spring, a coil spring, or a resilient living hinge) such that it is held in the closed position until sufficient force is exerted thereon to open the door (i.e., pivot it inward or outward). A used one of the needles 12' can be placed inside the chamber 70 by pressing on the door 74 with the instrument I and/or needle 12' held by the instrument, as shown in FIG. 2, releasing the needle so that it remains in the chamber, and withdrawing the instrument so that the door returns to the closed position with the used needle stored safely within the chamber. The door 74 is preferably positioned closer to one end of the housing 20 than the other so that there is room for all of the used sutures 14' in the chamber. The door 74, and thus the access opening formed when it is opened, is sized and shaped for receiving therethrough all of the needles 12 stored in the housing 20. In other embodiments, the door forms an access opening in the divider wall in other ways, for example, by at least a door portion of the divider wall sliding (e.g., co-planarly) relative to the housing. And in still other embodiments, the door is located in the housing at the outer wall section 26 so that the unused needles can be inserted into the chamber with the housing in the closed position. Preferably, the longitudinal ends of the housing comprise a pair of end tabs 80a-80d or flanges, one extending from each section of the clam-shell type housing. The flanges provide a grasping or gripping surface that the instrument I or other suitable instrument can grasp and manipulate the position of the housing. Preferably, the end tabs 80a-80d are rounded so as to not include any sharp edges. To open the housing 20, a practitioner uses a pair of instruments (such as robotic-assisted graspers or needle holders or conventional laparoscopic instruments) to individually grasp two opposing end tabs. By applying gentle opposing force to these two sections, the apparatus 10 opens.

Figure 3:
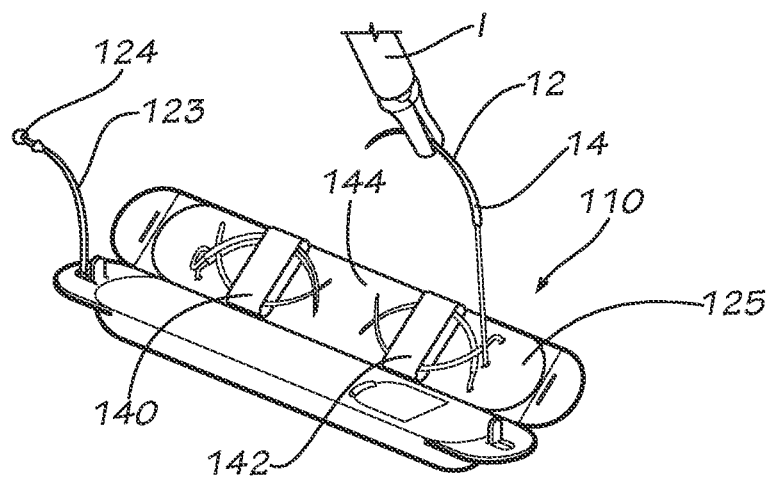
FIG. 3 is a perspective view of an apparatus for housing a plurality of needles according to another example embodiment of the present invention and shown in an open configuration.
Figure 4:
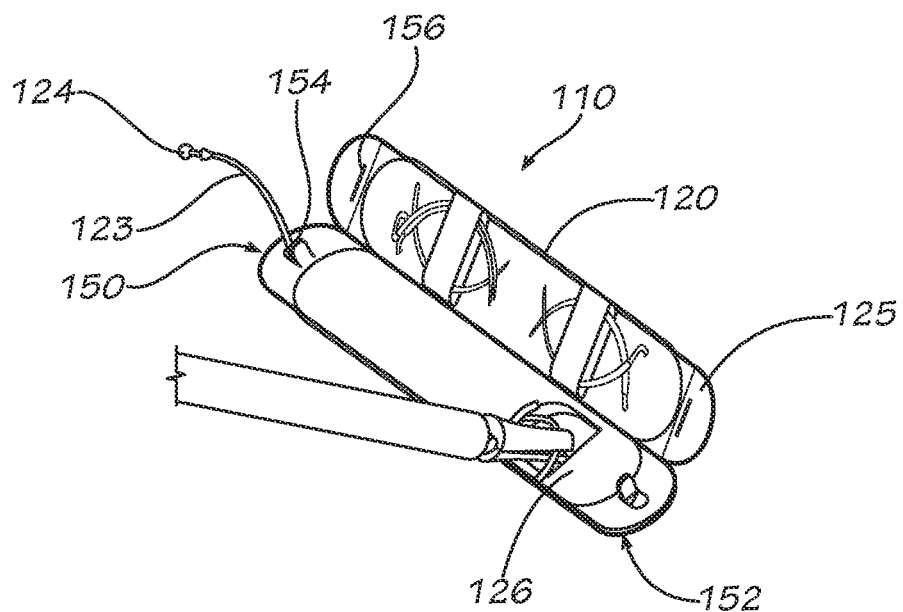
FIG. 4 is a perspective view of the apparatus of FIG. 3 and showing a used needle being placed inside a disposal portion of the apparatus.
Figure 5:
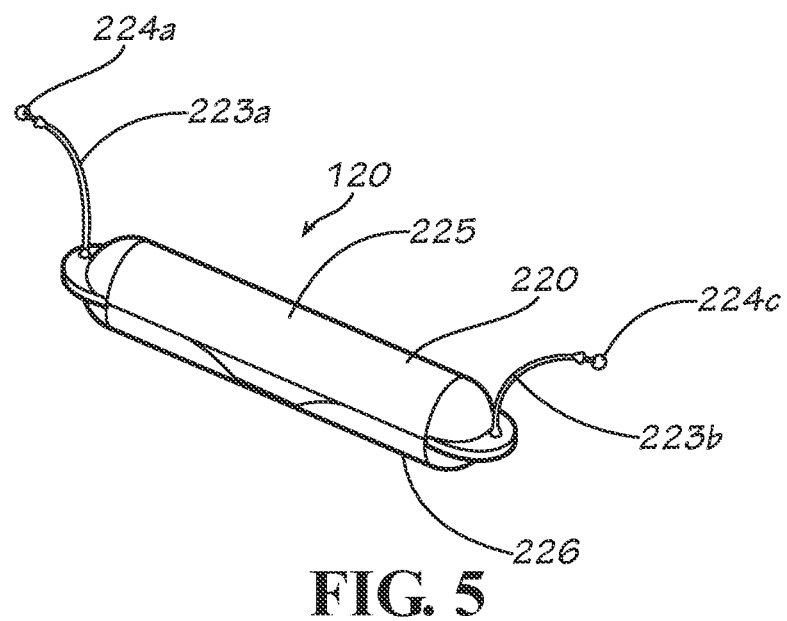
FIG. 5 is a perspective view of an apparatus for housing a plurality of needles according to another example embodiment of the present invention and shown in a closed configuration.

FIGS. 3-4 depict an apparatus 110 for holding a plurality of needles 12, each having an associated suture 14, according to another example embodiment. The apparatus 110 is substantially similar to the apparatus 10, but with the exceptions noted herein. The first section 125 of the housing 120 includes a pair of needle holders 140 and 142. Each of the needle holders 140 and 142 is configured to retain at least one and preferably a plurality of needles 12 with associated sutures 14. The needle holders 140 and 142 can comprise foam or silicone blocks into which the needles are secured, or they can comprise any other suitable tackable material. Although two such needles holders 140 and 142 are shown, any suitable number of needle holders can be employed. The associated sutures 14 can be attached to, secured within, or attached behind a foam bed 144 (such as in a manner similar to that described with reference to FIG. 1B), or they can be stored in any suitable manner within the first housing section 125.

Preferably, the apparatus 110 includes a locking mechanism to keep the housing 120 in its closed configuration until the practitioner opens the housing. For example, the apparatus 110 can include a pair of clasp locking members 150 and 152, one near each longitudinal end of the housing. A male portion 154 of the locking member can be located on the portion 126 of the housing 120 and a cooperating female portion 156 can be located on the other portion 125. When mated together, the male and female portions provide a lock to secure the housing in its closed configuration. To open the housing 120, a practitioner uses a pair of instruments (such as robotic-assisted graspers or needle holders or conventional laparoscopic instruments) to individually grasp the two edges of the locking mechanism. By applying gentle opposing force to these two edges, the male tabs resiliently deflect and the apparatus 110 opens. Alternatively, a magnetic lock, one portion on each section of the housing, is used to lock the housing in its closed configuration.

Figure 6:
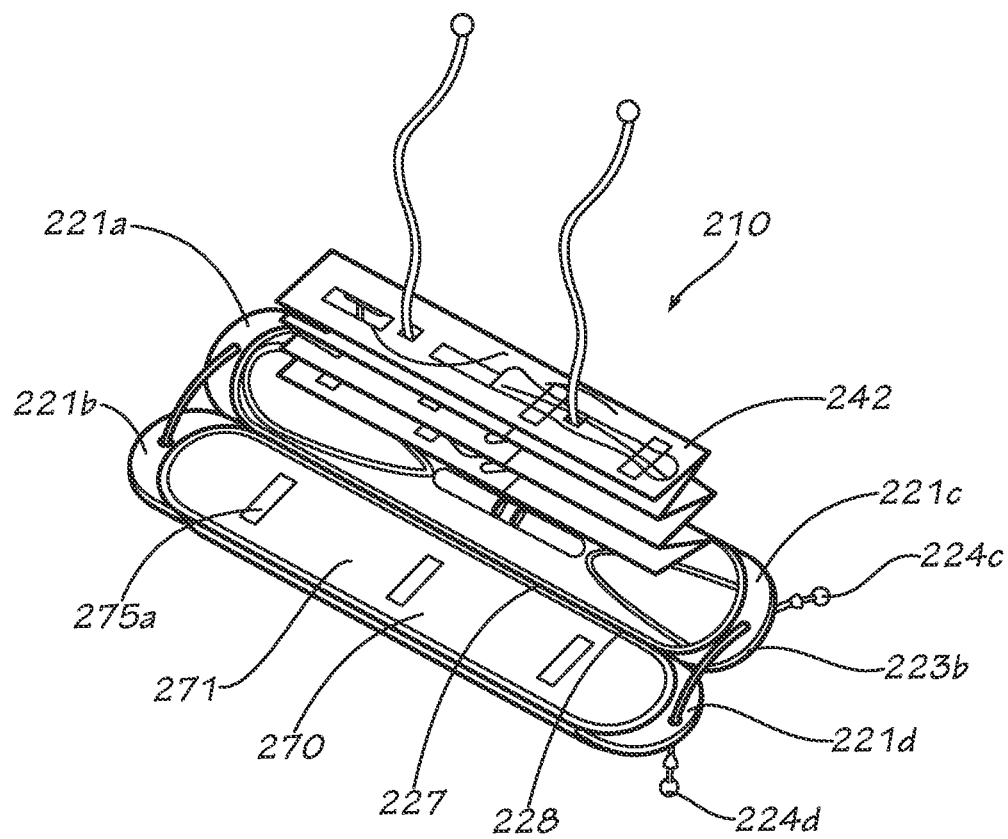
FIG. 6 is a perspective view of the apparatus of FIG. 5 shown in a partially open configuration.
Figure 7:
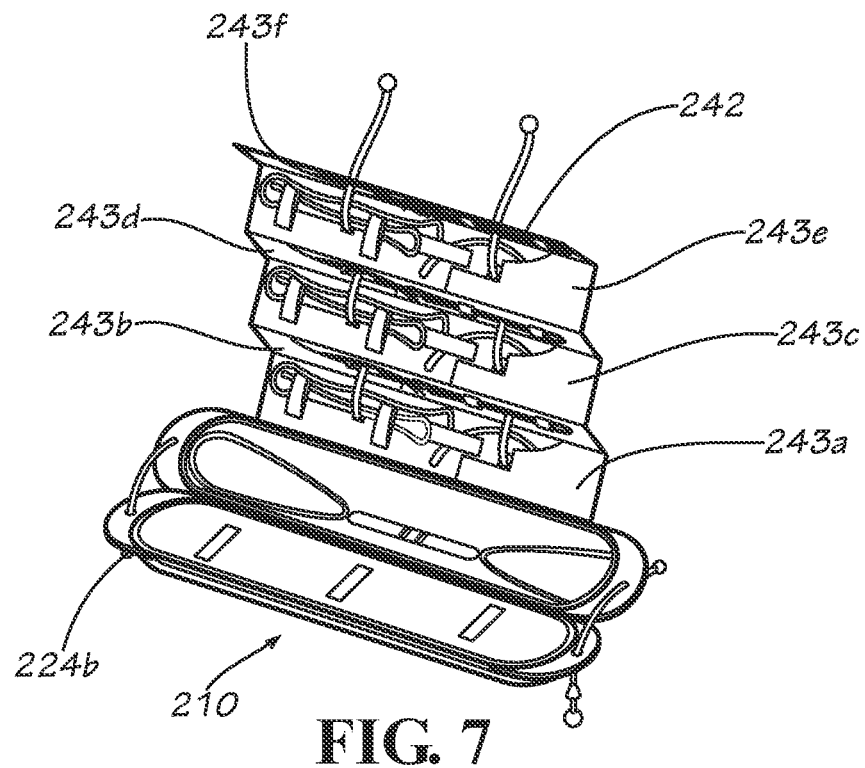
FIG. 7 is a perspective view of the apparatus of FIG. 5 shown in a first open configuration.
Figure 8:
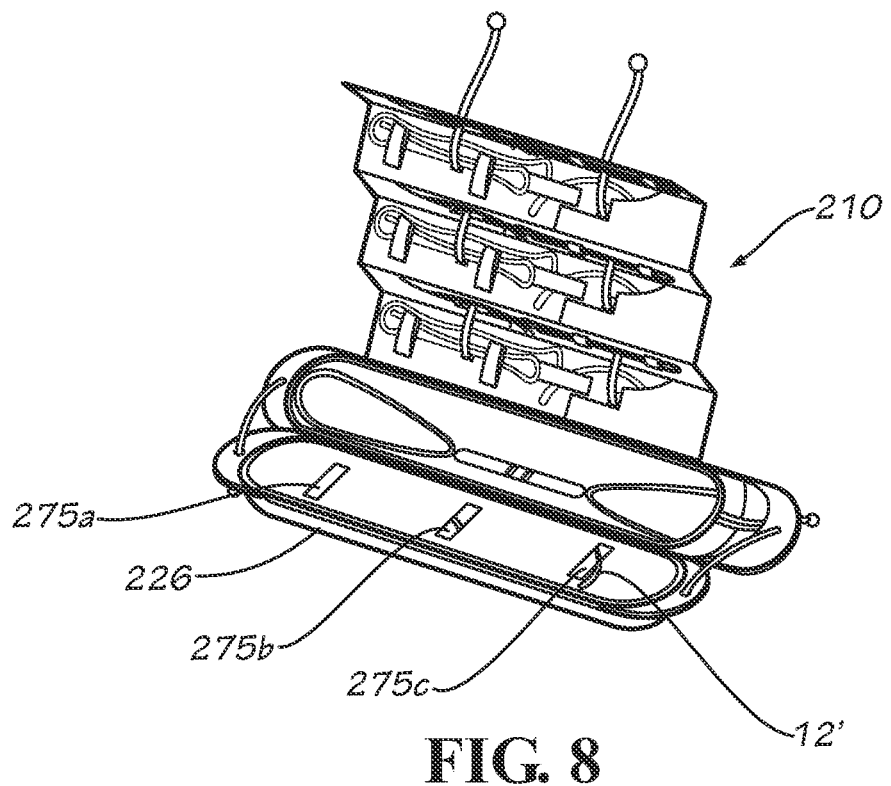
FIG. 8 is a perspective view of the apparatus of FIG. 5 shown in a second open configuration.

FIGS. 5-12 depict an apparatus 210 for holding a plurality of needles 12, each having an associated suture 14, according to another example embodiment. The apparatus 210 is substantially similar to the apparatus 10, but with the exceptions noted herein. The apparatus 210 comprises an elongated and generally cylindrical housing 220 that has a hinge 228 along a longitudinal edge 227 thereof. Preferably, the housing 220 is a substantially rigid clamshell-type housing such that once opened, the housing 220 comprises two halves or sections 225 and 226. Both sections 225 and 226 comprise end tabs or flanges 221a-221d extending from longitudinal ends thereof. The end tabs 221a-221d are preferably rounded. Each set of end tabs 221a, 221b and 221c, 221d comprise apertures that extend therethrough and that align when the housing 220 is in a closed configuration. One or more of the end tabs can be expandable or extendable/slidable along a longitudinal axis of the housing, as shown in FIG. 8. Such expandable feature provides greater accessibility to the needles 12 and sutures 14 therein.

A first tab cord 223a is inserted through the first set of tab apertures, and a second tab cord 223b is inserted through the second set of tab apertures located on the opposite end of the housing 220. Preferably, the tab cords 223a and 223b each comprise a stopper 224 near the free ends thereof that retain the cords 223a and 223b and prevent them from sliding through the apertures. The stoppers 224a-224d can include a plurality of conical and spherical shaped stoppers, although other suitably shaped stoppers can be employed as well. Thus, the tab cords 223a and 223b serve as a latch mechanism to open and close the housing and to keep the housing securely closed during insertion and removal of device from the subject. The stoppers 224a-224d also prevent the sections 225 and 226 from opening further than their intended opened angle (which is typically about 180°).

Figure 10:
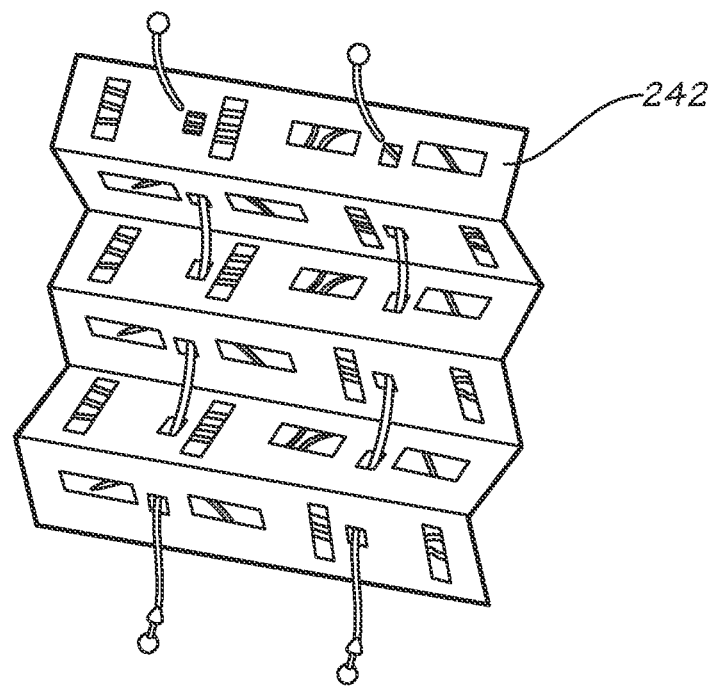
FIG. 10 is a rear perspective view of the folded panel needle holder portion of FIG. 9.

With reference now to FIG. 6, the housing 220 is shown in an open configuration. A folded needle holder panel 242 is mounted to the longitudinal free edge 229 of the section 225. However, in an alternative embodiment, the panel can be mounted to the hinged edge or to any suitable place along the body of the housing. Preferably, the panel 242 comprises a stiff material, such as a polymer or thin metal, although other suitable materials can be employed as well. The panel 242 comprises a plurality of segments 243, each of which comprises a plurality of combination suture and needle retainers 245 and a needle cover 250 for securely retaining a needle 12 with an associated suture 14. Although the depicted embodiments shows six such segments 243a-243f, the panel 242 can comprise any suitable number of segments. The panel sections can be folded in order to create an accordion-like design. As shown in more detail in FIGS. 11-12, each needle retainer 245 generally comprises a pair of parallel slits that form a strip in the panel. For example, a pair of longitudinally elongated strips 247a and 247b can retain the needle, and another pair of strips 249a and 249b can retain the suture in an organized manner. Preferably, the needles 12 and sutures 14 are held such that extracting a needle 12 and its associated suture 14 from the retainers 245 is simple and efficient with no knotting or tangling of the suture 14 (i.e., the suture is wound or folded in a predetermined configuration to avoid knotting and tangling with itself and the other sutures). In the depicted embodiment, the needle cover 250 comprises a generally longitudinal extension of the panel section or flap, which covers the sharp tip of the needle. The needle cover 250 can be unfolded to expose the needle 12 and allow the needle 12 to be extracted from the panel 242, as shown in FIG. 10. As depicted in FIGS. 7-8, the needles can be arranged such that the tips of adjacent needles are positioned at the opposite lateral edges of the panel. In other embodiments, the tips of all needles can be positioned along the same side of the panel, or they each can be positioned at any suitable location along the panel.

Figure 9:
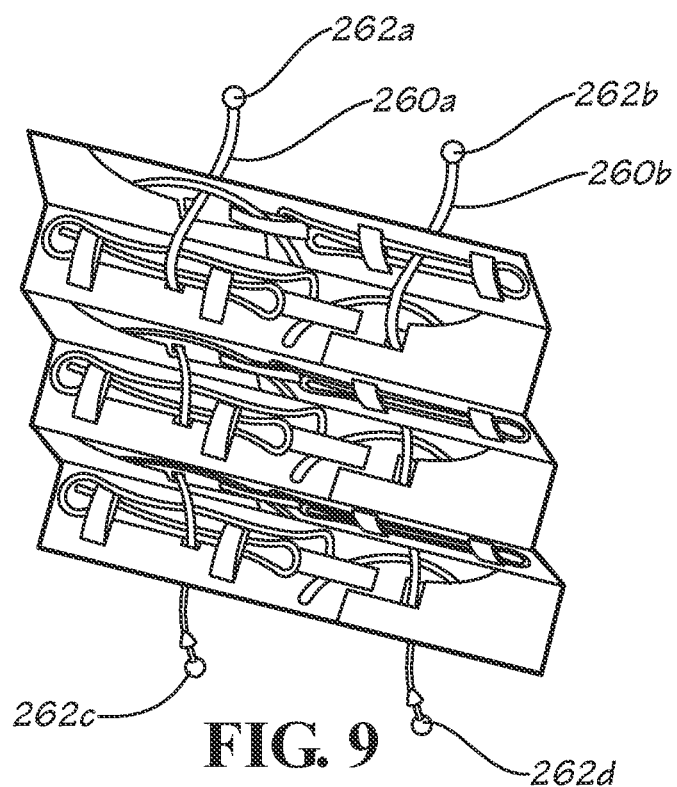
FIG. 9 is a front perspective view of a folded panel needle holder portion of the apparatus of FIGS. 5-8.

In this embodiment of FIGS. 5-12, the panel can be expanded and collapsed by grasping a pair of panel cords 260a and 260b (such as with the instrument), although in an alternative embodiment, a single tab cord can be employed. Preferably, the panel cords 260a and 260b are constructed of a flexible, biocompatible material. The panel cords 260a and 260b are inserted through the apertures in the six sections 243a-243f of the panel that are arranged to provide a generally linear pathway for the panel cords 260a and 260b. As best seen in FIGS. 9-10, at the distal ends of the panel cords 260a and 260b are panel cord stoppers 262a-262d, dimensioned to be large enough to prevent the cords from sliding through the apertures of the folded panel. Preferably, the panel cord stoppers 262a-262d are constructed of a substantially rigid material that cannot be pulled through the apertures. Preferably, the cords 260a and 260b can extend through the panel 242 and are not secured to the housing 220, as shown in the panel views of FIGS. 9-10. Alternatively, the proximal ends of the panel cords 260a and 260b can be attached to the panel 242 or to the housing 220. The cords 260a and 260b can also provide a guide for the panel 242 to unfold along. In other words, the instrument I can grasp and unfold the panel 242 along the panel cords 246. Additionally or alternatively, the panel 242 can also be unfolded by also grasping the panel 242 (by the practitioner or through the use of the instrument I) and any other suitable part of the apparatus 210 and expanding the panel outwardly.

Figure 14:
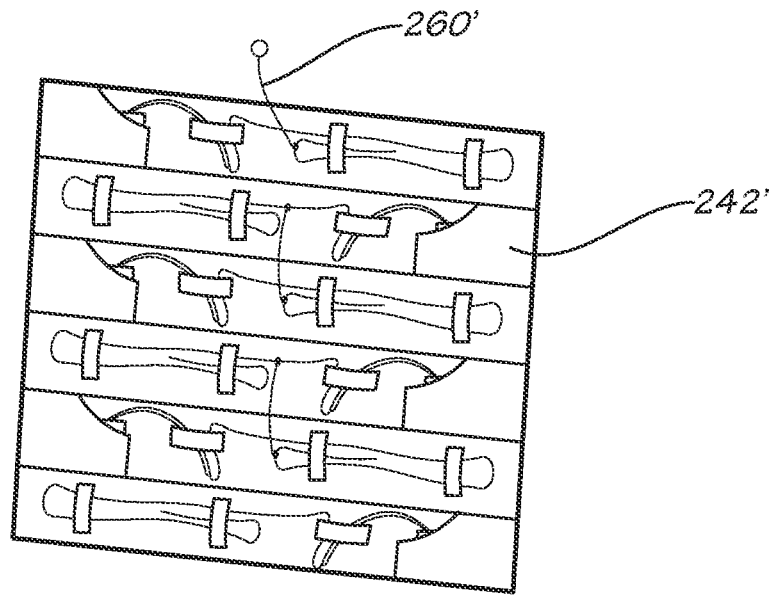
FIG. 14 is a front perspective view of a folded panel needle holder portion according to an alternative embodiment.
Figure 15:
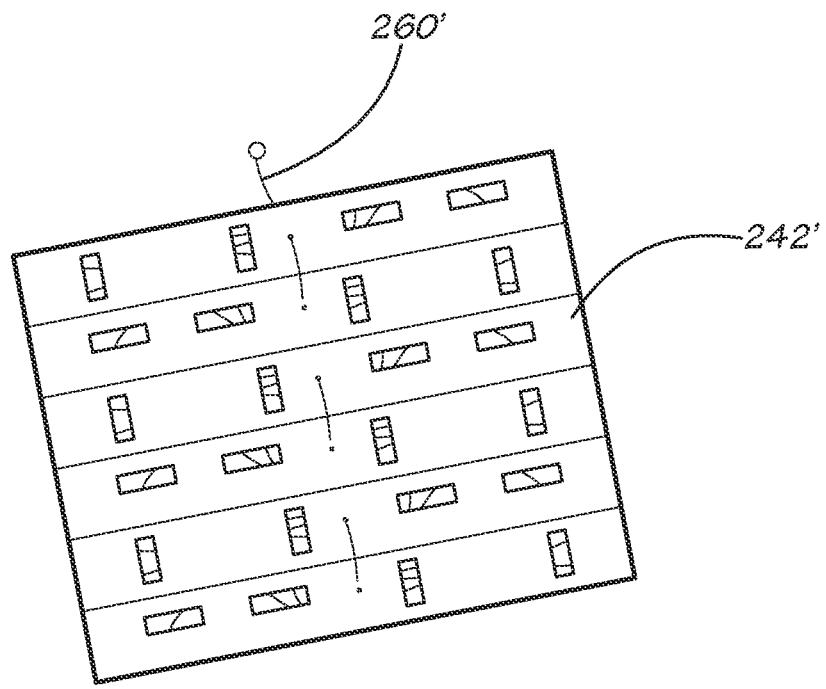
FIG. 15 is a rear perspective view of the folded panel needle holder portion of FIG. 14.

In an alternative embodiment, a single panel cord 260a' extending through the segments 243' of the panel 242', as shown in FIGS. 14-15, can be used in lieu of the pair of panel cords 260. Moreover, in other alternative embodiments, three or more cords can be employed.

Figure 11:
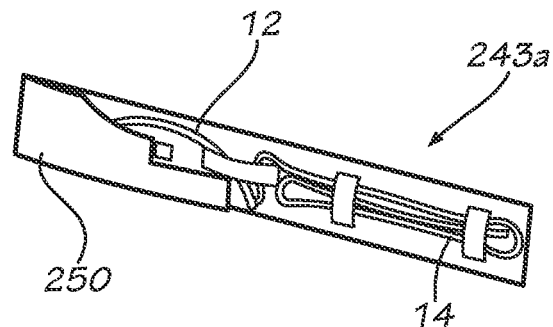
FIGS. 11 is a front perspective view of one segment of a needle holder portion of the panel of FIGS. 9-10.
Figure 12:
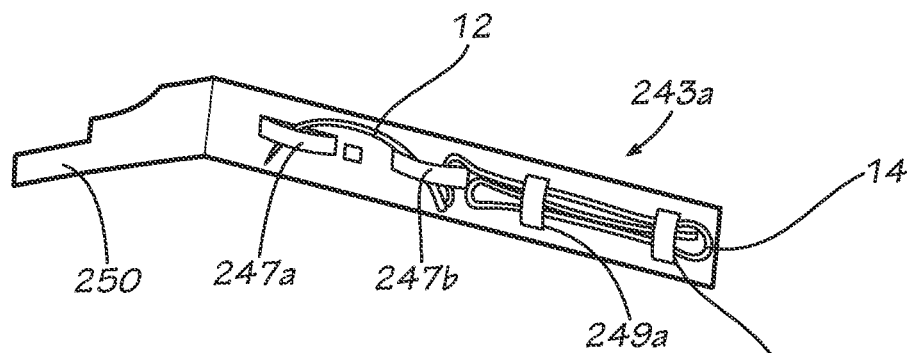
FIGS. 12 is a front perspective view of one segment of a needle holder portion of the panel of FIGS. 9-10 and shown with a needle cover portion in an open configuration.
Figure 13:
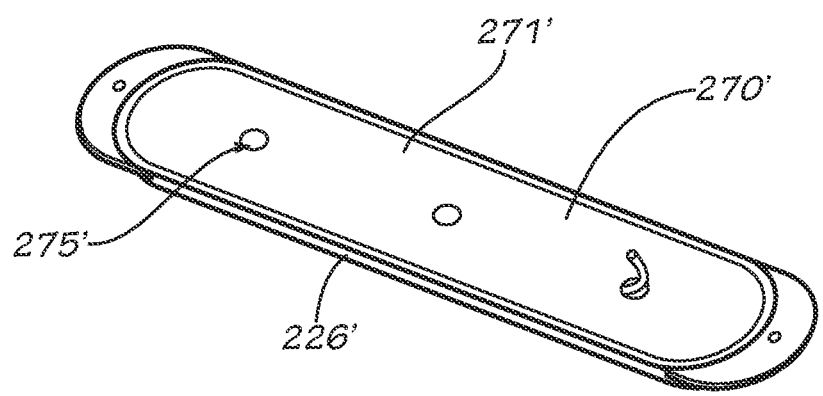
FIG. 13 is a perspective view of a needle disposal portion of an apparatus for housing a plurality of needles according to another embodiment of the present invention.

Referring back to FIGS. 6-10, the housing 220 further includes an enclosed disposal chamber 270 within the second section 226. The generally semi-cylindrical outer wall 276 of the second section 226 of the housing and a flat upper wall 271 define the enclosed disposal chamber. The upper wall 271 includes a plurality of chamber apertures 275 extending therethrough. The apertures 275 are suitably sized and shaped to allow a used needle with any remaining suture length to be inserted therethrough and into the disposal chamber, as shown in FIG. 8. As shown, the chamber apertures 275 are rectangular-shaped, although in alternative embodiments, other shapes can be employed. For example, a plurality of apertures 275' extending through the upper wall 271' of the generally enclosed chamber 270' of the second section 226' of the housing 220' have a round shape, as shown in the alternative embodiment of FIG. 11. Although three such apertures are shown in FIGS. 8 and 11, fewer (including a single aperture) or more apertures can be included in the upper wall 271 or 271'.

Figure 16:
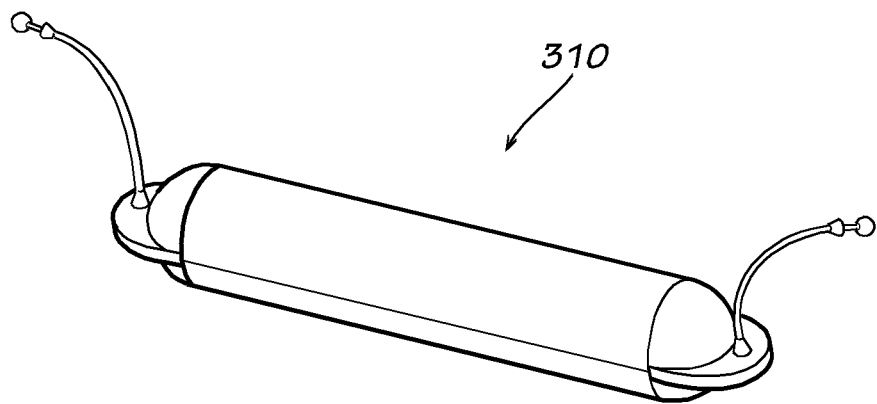
FIG. 16 is a perspective view of an apparatus for housing a plurality of needles according to another example embodiment of the present invention and shown in a closed configuration.
Figure 17:
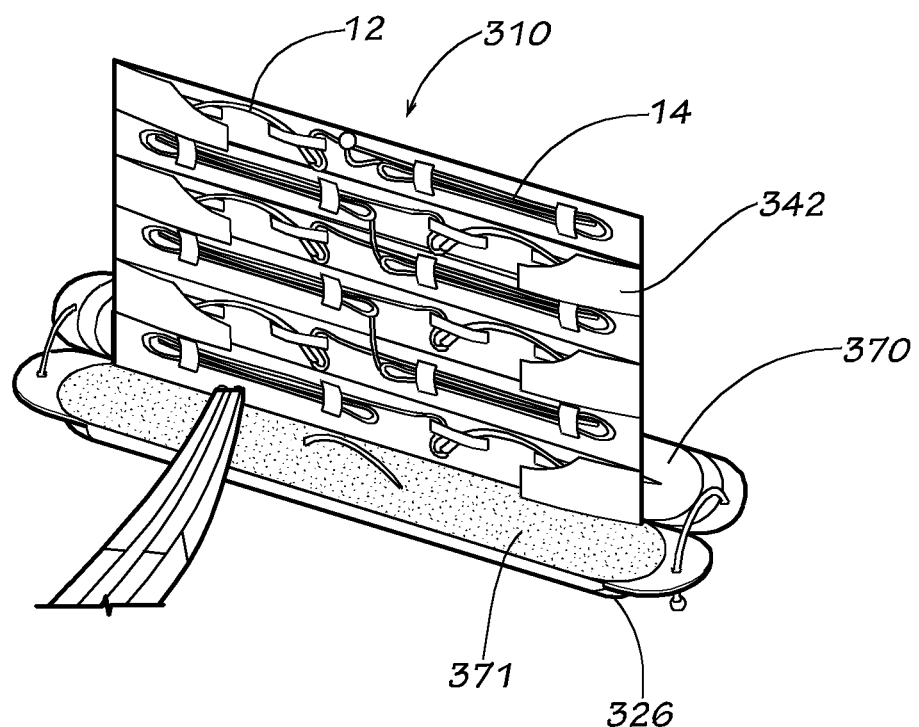
FIG. 17 is a perspective view of the apparatus of FIG. 16 and shown in an open configuration.
Figure 18:
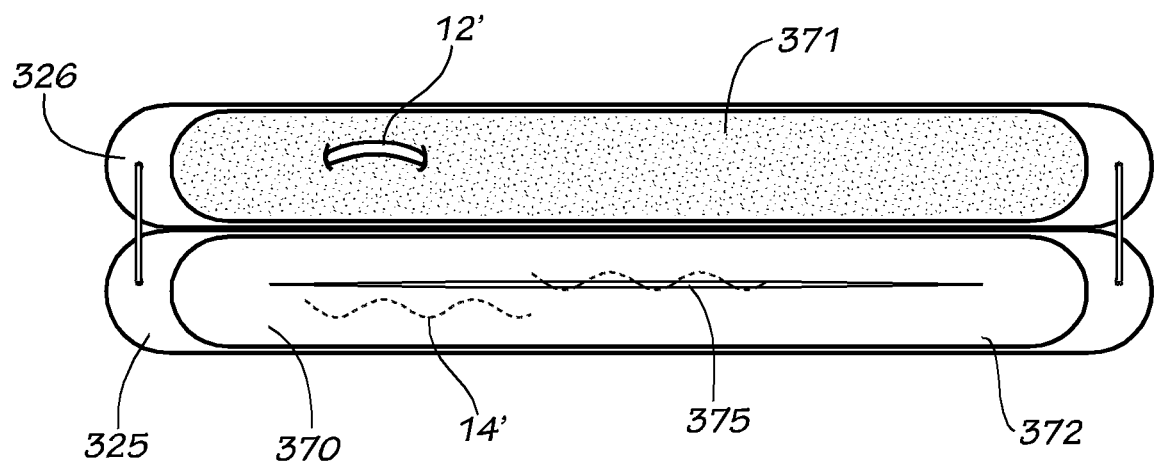
FIG. 18 is a perspective view of the apparatus of FIG. 16 and shown in an open configuration with a folded panel holder portion removed (for purposes of clarity).

FIGS. 16-18 depict an apparatus 310 having a folded panel 342 for housing a plurality of needles 12, each having an associated suture 14, according to another example embodiment. FIG. 18 shows a perspective view of the apparatus 310 with the needle panel 342 omitted for clarity. The apparatus 310 is substantially similar to the apparatus 110, but with the exceptions noted herein. The apparatus 310 includes a panel 342, which is substantially similar to the panel 242, attached to the hinged longitudinal edge 327 of one section of the housing 320. Alternatively, the panel 342 can be attached to the hinge 328 of the housing or to a free lateral edge of one section of the housing.

The apparatus 310 includes an enclosed suture disposal chamber 370 within a first section 325 of the clam-shell type housing 320 and a foam bed 371 within a second section 326 of the housing. Preferably, the disposal chamber 370 comprises a flexible cover 372 formed of any suitable material with a slit 375 extending along substantially the length of the cover. The cover 372 can be constructed of any suitable material, such as but not limited to a polymer. The slit 375 is configured to receive remaining unused portions of used sutures 14' (and optionally used needles) therethrough. In alternative embodiments, the slit 375 can be longer or shorter or multiple slits can be employed. In still alternative embodiments, the cover can be substantially inflexible or rigid with an elongated opening of sufficient width to receive the used needles. Preferably, the remaining suture portions 14' are housed within the suture disposal chamber 370, while the used needles 12' are tacked in the foam bed 371. However, used needles can optionally be stored within the suture disposal chamber 370 or both the used needles and sutures can be tacked into the foam bed 371.

Figure 19:
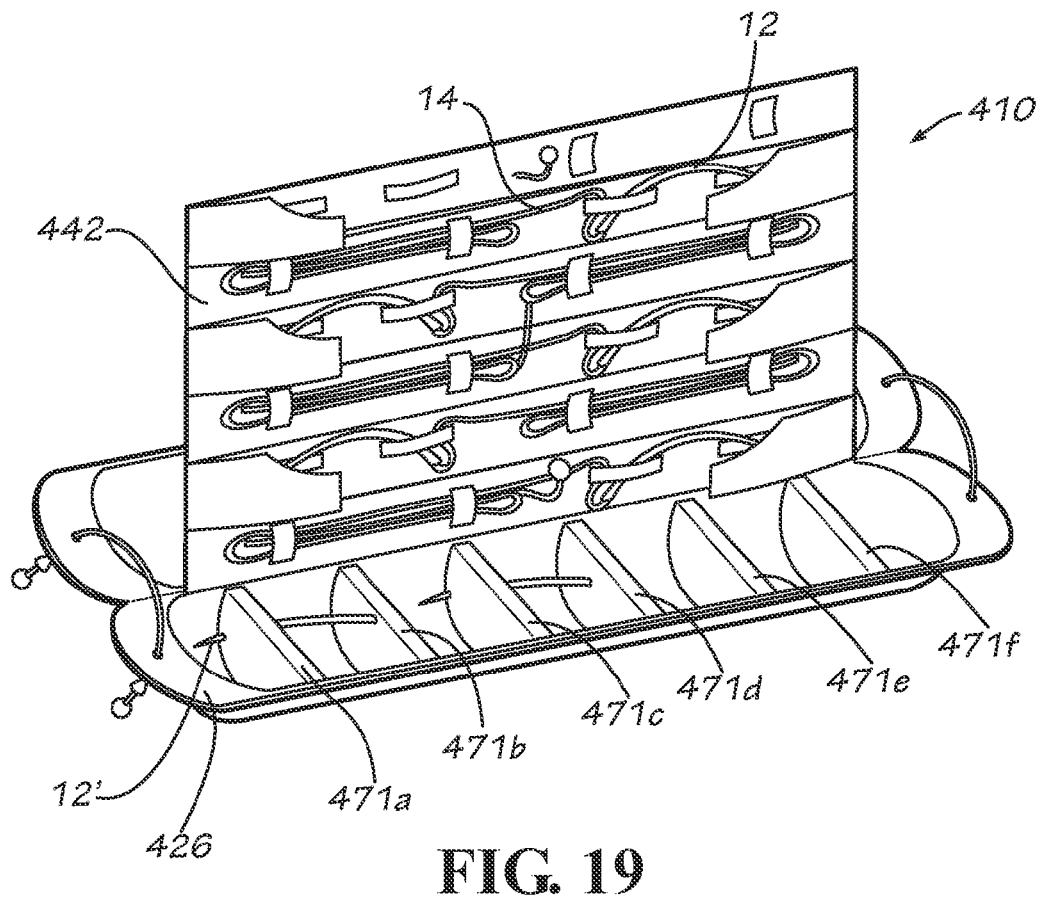
FIG. 19 is a perspective view of an apparatus for housing a plurality of needles according to another example embodiment of the present invention and shown in an open configuration.
Figure 20:
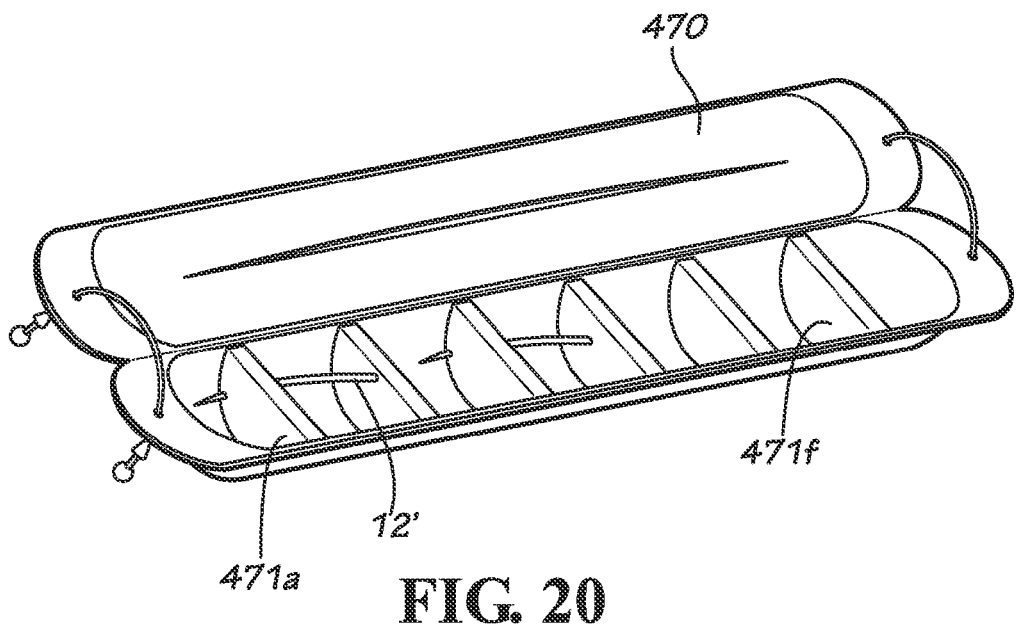
FIG. 20 is a perspective view of the apparatus of FIG. 19 and shown in an open configuration with a folded panel holder portion removed (for purposes of clarity).

FIGS. 19-20 depict an apparatus 410 for housing a plurality of needles 12, each having an associated suture 14, according to another example embodiment. FIG. 20 shows a perspective view of the apparatus 410 with the needle panel 442 omitted for clarity. The apparatus 410 is substantially similar to the apparatus 310 but with the exceptions noted herein. In this embodiment, the foam bed for needle disposal has been replaced by a plurality of semicircular disposal walls 471a-471f conforming and secured to the housing section 426. Six such disposal walls 471a-471f are shown, although the housing can comprise any suitable number of disposal walls. Each disposal wall 471a-471f can be configured to retain a single used needle 12', or each disposal wall can be configured to retain a plurality of used needles. Preferably, the walls 471 are formed of foam or another suitable material for securing (or "tacking") the needles 12' thereto. Thus, used needles 12' can be tacked into the foam walls 471a-471f after their use, while the used sutures can be stored in the suture disposal chamber 470 (which is substantially similar to the chamber 370).

Figure 21:
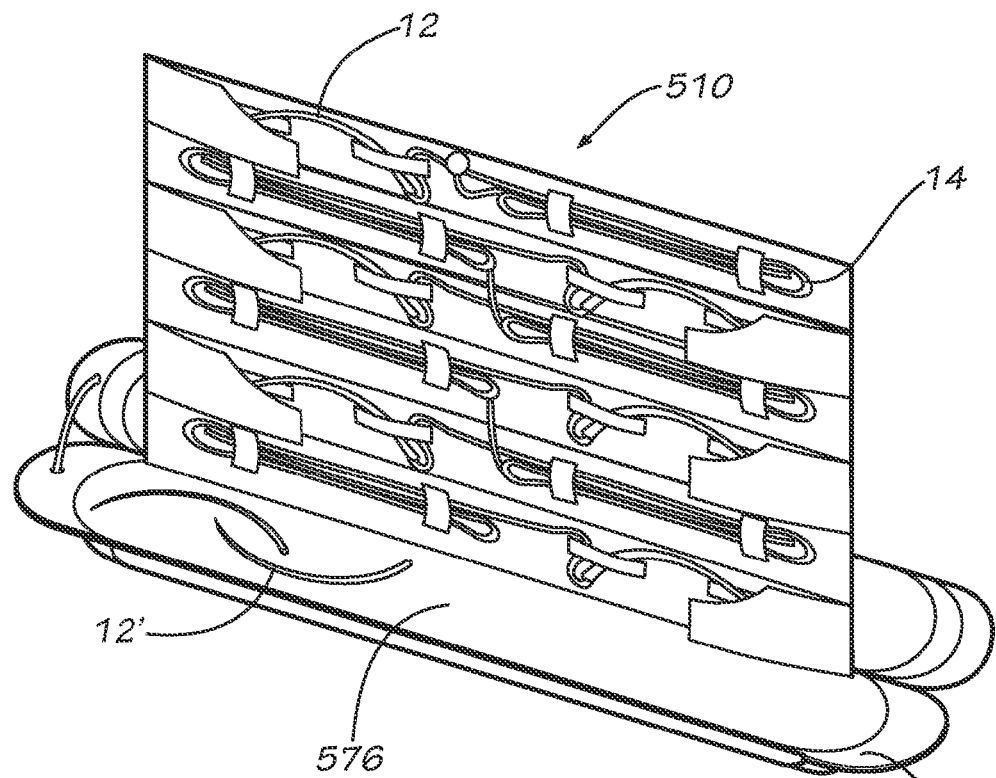
FIG. 21 is a perspective view of an apparatus for housing a plurality of needles according to another example embodiment of the present invention and shown in an open configuration.
Figure 22:
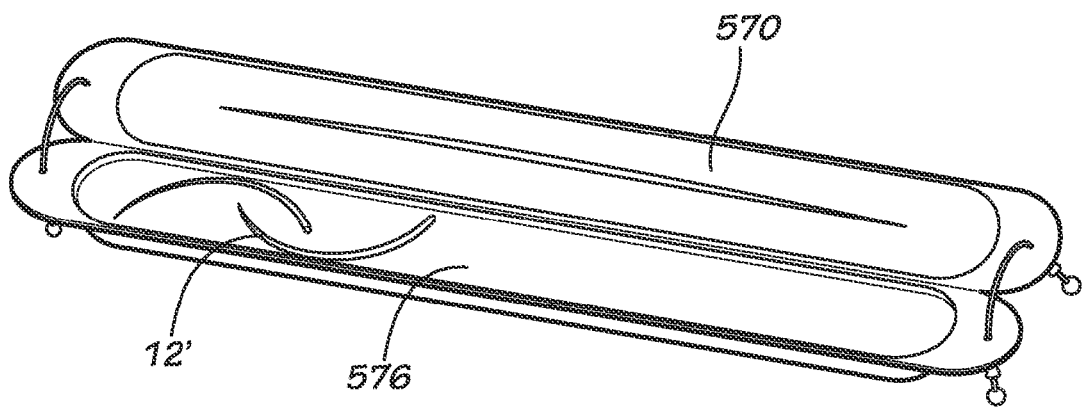
FIG. 22 is a perspective view of the apparatus of FIG. 21 and shown in an open configuration with a folded panel holder portion removed (for purposes of clarity).

FIGS. 21-22 depict an apparatus 510 for housing a plurality of needles 12, each having an associated suture 14, according to another example embodiment. FIG. 22 shows a perspective view of the apparatus 510 with the needle panel omitted for clarity. The apparatus 510 is substantially similar to the apparatus 310, but with the exceptions noted herein. In this embodiment, the housing section 526 includes a magnet or a magnetic bed 576 for retaining used metal needles 12'. The magnetic bed 576 can be one continuous magnet or can include a plurality of small magnets. Thus, used needles 12' can be magnetically adhered or attached to the magnetic bed 576, while the used sutures can be stored in the suture disposal chamber 570 (which is substantially similar to the chamber 370).

Figure 23:
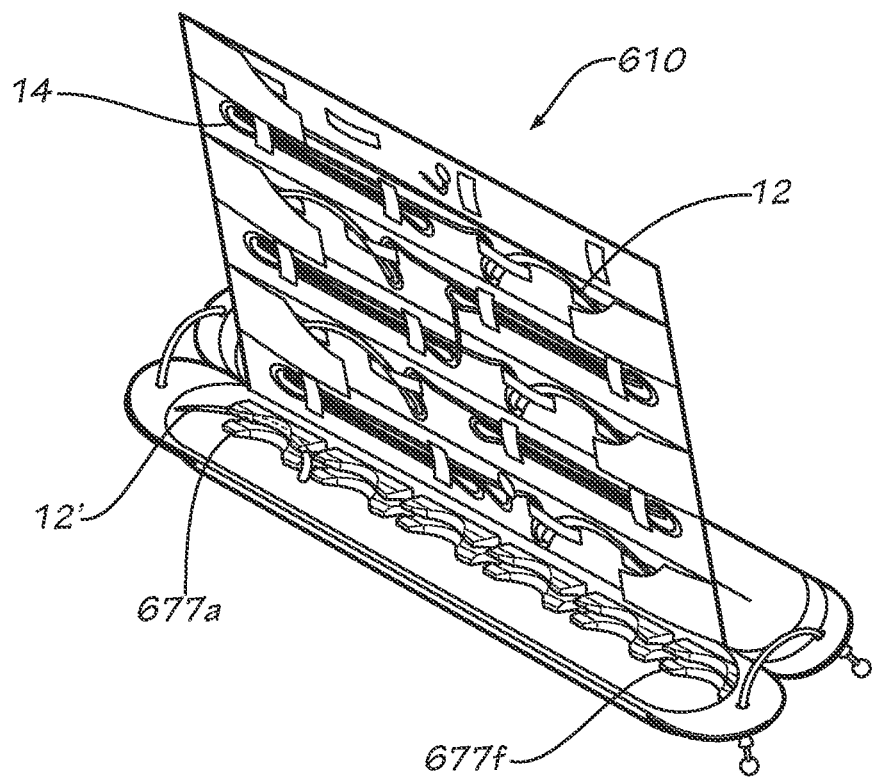
FIG. 23 is a perspective view of an apparatus for housing a plurality of needles according to another example embodiment of the present invention and shown in an open configuration.
Figure 24:
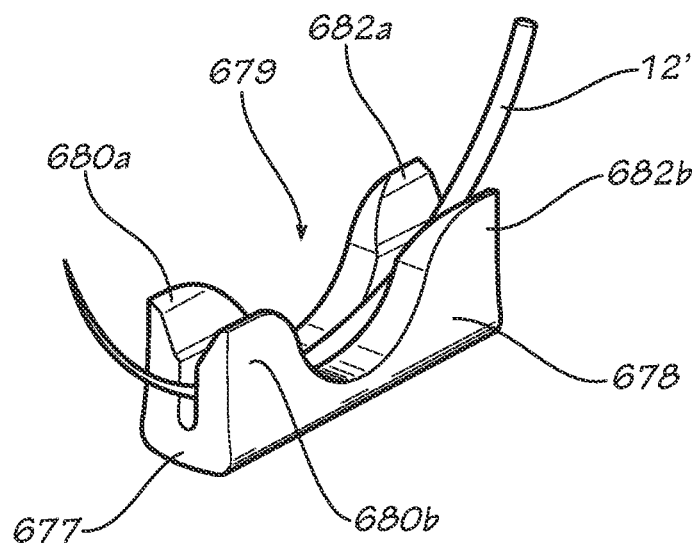
FIG. 24 is a perspective view of a needle clip portion of the apparatus of FIG. 23.
Figure 25A:
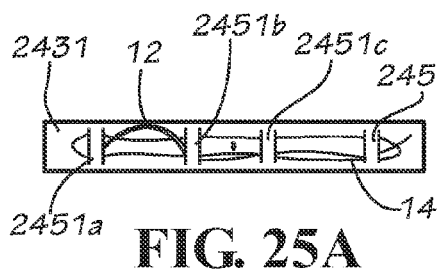
FIGS. 25A and 25B depict front and rear views, respectively, of one configuration for a segment of a folded panel holder portion of an apparatus for housing a plurality of needles according to an example embodiment of the present invention.
Figure 25B:
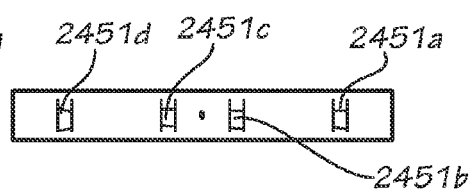
Figure 26A:
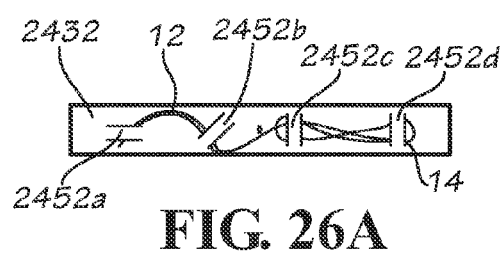
FIGS. 26A and 26B depict front and rear views, respectively, of another configuration for a segment of a folded panel holder portion of an apparatus for housing a plurality of needles according to an example embodiment of the present invention.
Figure 26B:
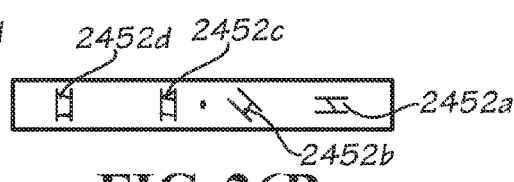
Figure 27A:
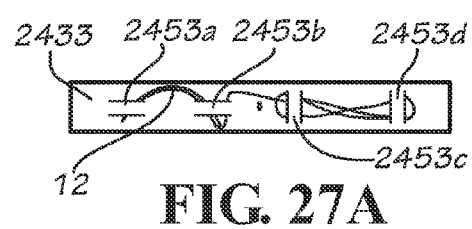
FIGS. 27A and 27B depict front and rear views, respectively, of another configuration for a segment of a folded panel holder portion of an apparatus for housing a plurality of needles according to an example embodiment of the present invention.
Figure 27B:
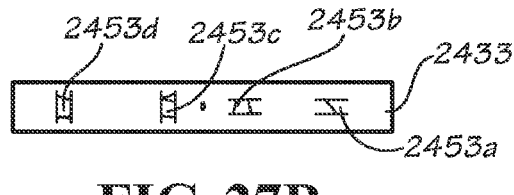
Figure 28A:
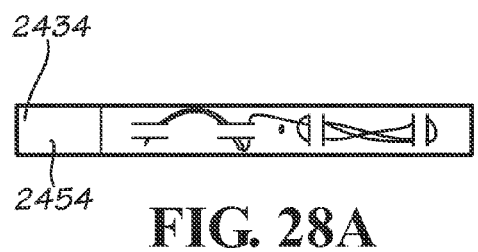
FIGS. 28A and 28B depict front and rear views, respectively, of another configuration for a segment of a folded panel holder portion of an apparatus for housing a plurality of needles according to an example embodiment of the present invention.
Figure 28B:
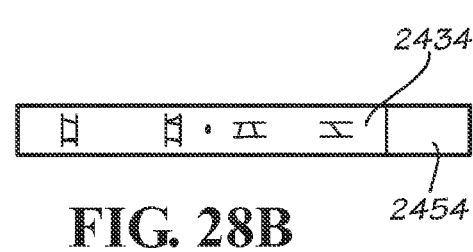
Figure 29A:
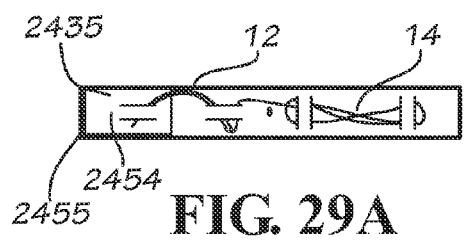
FIGS. 29A and 29B depict front and rear views, respectively, of another configuration for a segment of a folded panel holder portion of an apparatus for housing a plurality of needles according to an example embodiment of the present invention.
Figure 29B:
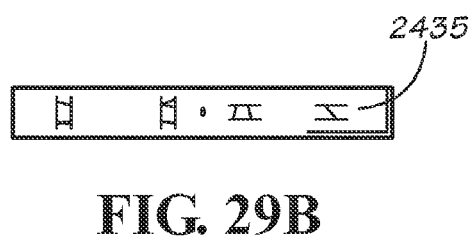

FIGS. 23-24 depict an apparatus 610 for housing a plurality of needles 12, each having an associated suture 14, according to another example embodiment. The apparatus 610 is similar to the apparatus 310 but with the exceptions noted herein. The foam bed for needle disposal has been replaced by a plurality of disposal needle clips 677a-677f secured within the housing section 626. Each clip 677a-677f is configured to retain a single used needle 12', although in alternative embodiments, a single clip can retain a plurality of used needles. As shown in FIG. 24, each needle clip 677 comprises a clip body 678, a receiving groove 679 therein, and two pairs of clip arms 680a, 680b and 682a, 682b. The clip 677 of the depicted embodiment is generally C-shaped so as to conform to the generally C-shaped needle, however, the clip can have other suitable shapes and sizes. Optionally, the clip arms 680a, 680b and 682a, 682b can have chamfered or flared edges to help guide a used needle 12' into the clip. Preferably, each needle clip 677 is constructed so that an instrument holding a used needle 12' can easily engage and slide the used needle 12' within the clip arms 680 and clamp the used needle 12' therein. The clip 677 can be constructed of a resilient material, such as but not limited to foam, plastic, or metal. However, any other suitable material can be employed.

FIGS. 25-29 depict front and rear views of possible configurations of the panel segments for use with any of the panels of the present invention. The front view is shown in the "A" figures, and the rear view is shown in the "B" figures. The retainers for holding the needles and the sutures are pairs of parallel slits, and several different possible configurations are shown in FIGS. 25A-29B, although other suitable configurations can be employed as well. The panel section 2431 shown in FIGS. 25A and 25B has four pairs of parallel slits, each pair defining a strip 2451a-2451d aligned in a generally vertical orientation. A needle 12 can be placed behind the strips 2451a-2451d to hold the needle against the front surface of the panel segment 2431. Panel section 2432, as shown in FIGS. 26A and 26B, has four pairs of parallel slits defining strips 2452a-2452d positioned in the general fashion as shown, with the needle 12 and its associated suture 14 inserted therethrough. A needle 12 can be placed behind the strips 2452a-2452d to hold the needle against the front surface of the panel segment 2432. Panel section 2433, as shown in FIGS. 27A and 27B, has four pairs of parallel slits defining strips 2453a-2453d positioned in the general fashion as shown, with the needle 12 and its associated suture 14 inserted therethrough. A needle 12 can be placed behind the strips 2453a-2453d to hold the needle against the front surface of the panel segment 2433. Panel section 2434, as shown in FIGS. 28A and 28B, is substantially similar to the panel section 2433 but includes an additional flange or flap portion 2454 that is folded over the needle tip, thereby providing a needle cover. Panel section 2435, as shown in FIGS. 29A and 29B, is substantially similar to panel section 2434, but the needle cover flap 2454 folded over the needle is sealed with a glue line 2455 or other suitable adhesive or known fastener along two sides. The glue line 2455 keeps the needle cover 2454 folded over the needle 12.

Figure 30:
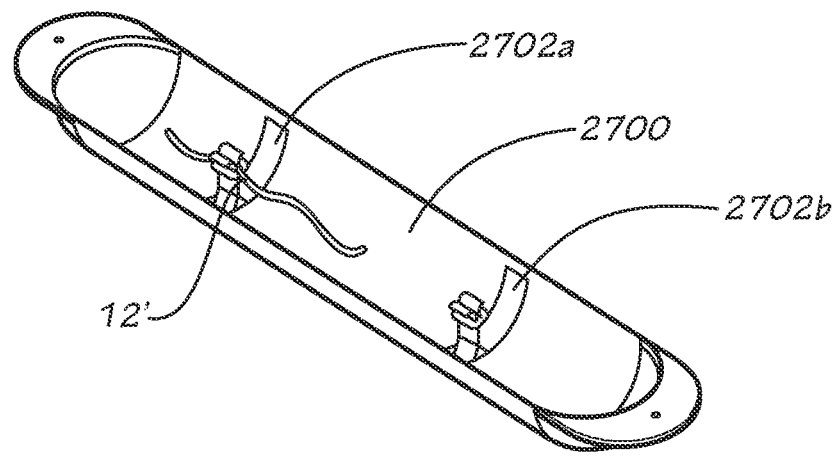
FIG. 30 is a perspective view of a needle disposal portion of an apparatus for housing a plurality of needles according to an example embodiment of the present invention.
Figure 31:
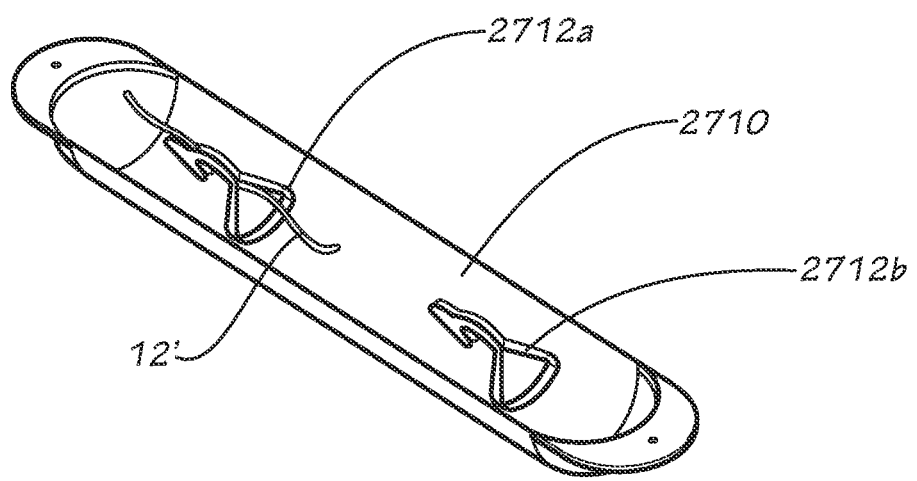
FIG. 31 is a perspective view of a needle disposal portion of an apparatus for housing a plurality of needles according to another example embodiment of the present invention.

FIGS. 30-31 show example embodiments of two needle disposal portions 2700 and 2710 for use with any of the apparatuses discussed herein. The needle disposal portion 2700 of FIG. 30 includes clips 2702a and 2702b. The needle disposal portion 2710 of FIG. 31 includes clips 2712a and 2712b. The clips 2702a, 2702b and 2712a, 2712b function in a similar manner to the clips 677 of FIGS. 23-24 to securely retain a used needle 12' and/or suture therein. Each clip can be configured to hold a plurality of needles and/or sutures, or they can be configured to hold a single needle and/or suture. Although two such clips are shown, any suitable number and types of clips can be employed. Additionally, the clips can be constructed of any suitable material.

Figure 32:
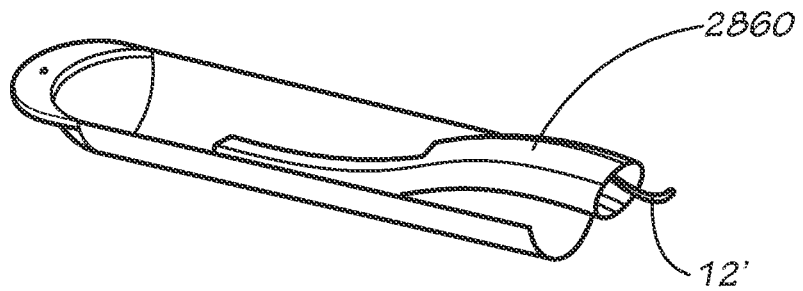
FIG. 32 is a cutaway perspective view of a disposal portion of an apparatus for housing a plurality of needles according to an example embodiment of the present invention and showing a needle bag in an open configuration.
Figure 33:
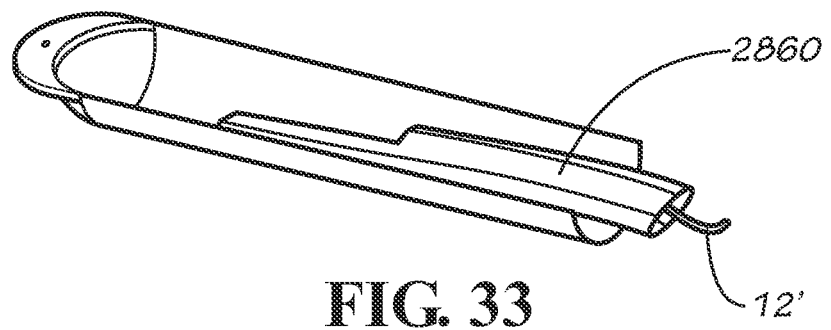
FIG. 33 is a cutaway perspective view of the disposal portion of FIG. 32 and showing the needle bag in a closed configuration.
Figure 34:
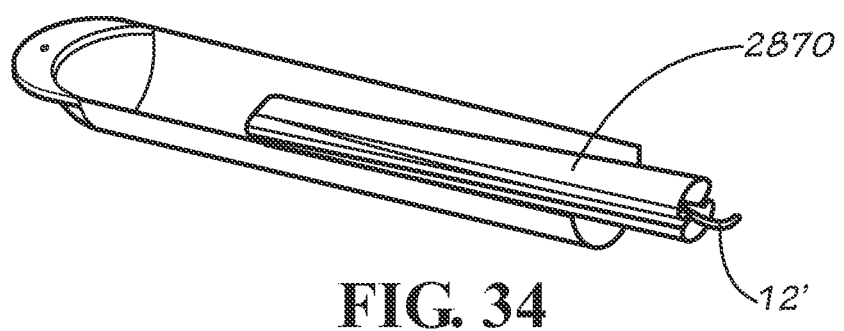
FIG. 34 is a cutaway perspective view of a disposal portion of an apparatus for housing a plurality of needles according to another example embodiment of the present invention and showing a needle bag in an open configuration.
Figure 35:
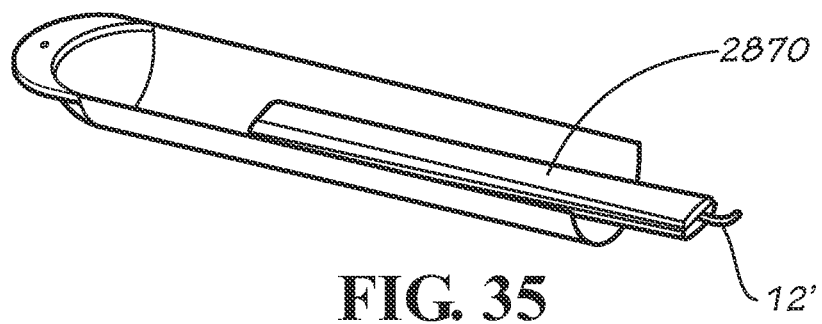
FIG. 35 is a cutaway perspective view of the disposal portion of FIG. 34 and showing the needle bag in a closed configuration.

FIGS. 32-35 show cutaway views of two example embodiments of a needle bag or pouch 2860 for use with any of the apparatuses discussed herein. FIG. 32 shows a disposal bag 2860 in a partially open configuration, while FIG. 33 shows the bag 2860 in a somewhat closed configuration. The bag 2860 is a generally elongated bag (or pouch) with one closed end and is sized and shaped to fit within one section of the housing (i.e., fit within the disposal section of the housing). An opening at the opposite end thereof receives used needles 12' and used sutures. The bag 2860 can be made of a plastic or any other suitable material. FIGS. 34-35 depict a bag 2870 that is substantially similar to the bag 2860, with the exception that the bag 2870 is gusseted.

Figure 36:
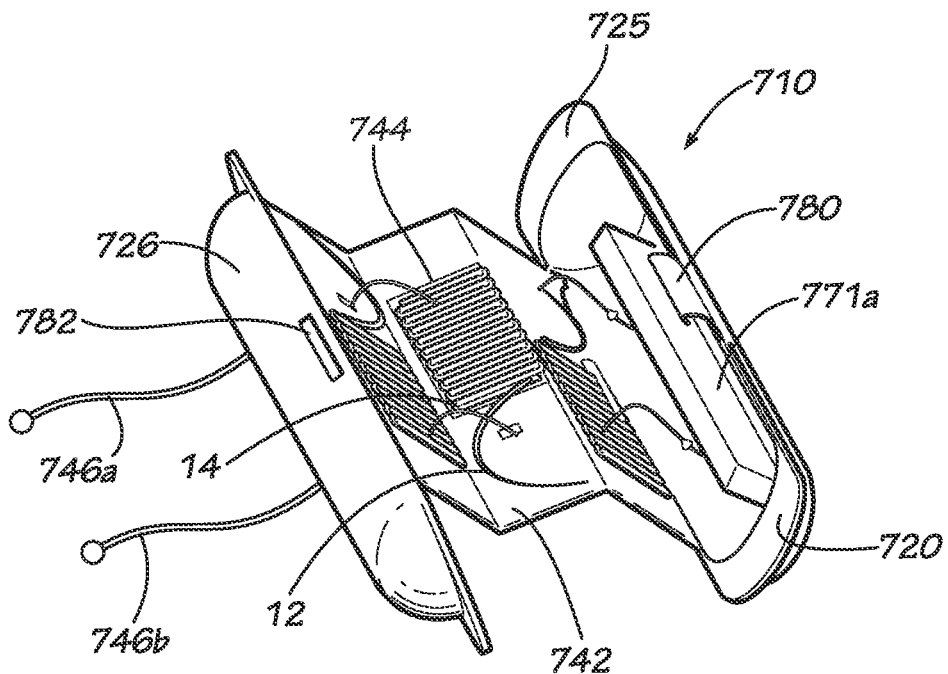
FIG. 36 is a front perspective view of an apparatus for housing a plurality of needles according to another example embodiment and shown in an open configuration.
Figure 37:
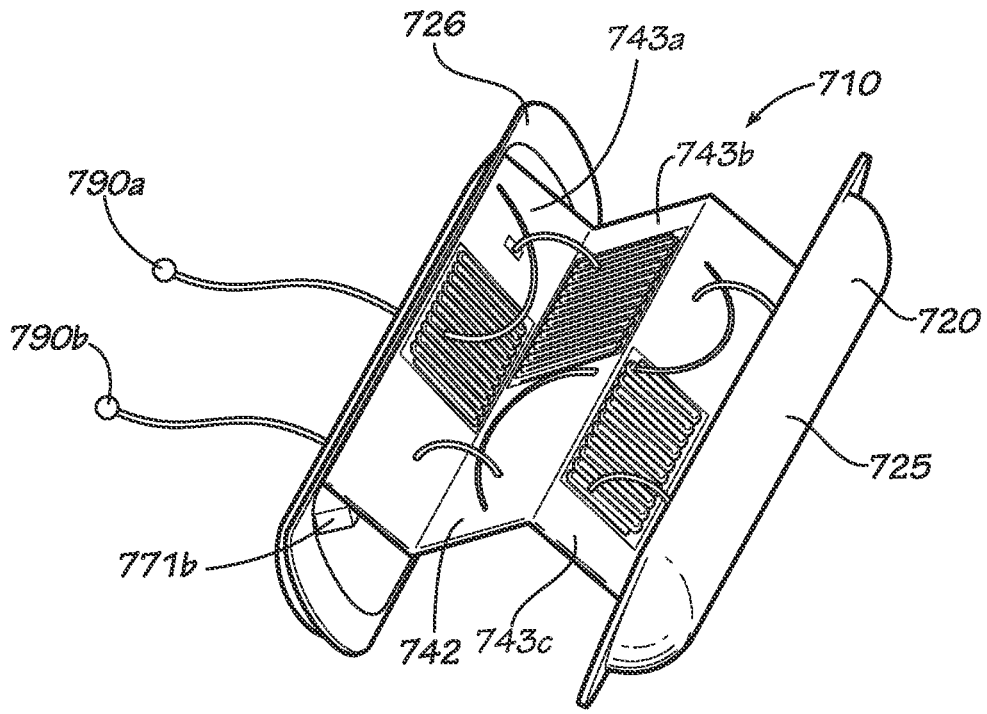
FIG. 37 is a rear perspective view of the apparatus of FIG. 36 and shown in an open configuration.

FIGS. 36 and 37 show an apparatus 710 for housing a plurality of needles 12, each having an associated suture 14, according to another example embodiment. This apparatus 710 comprises a generally cylindrical housing 720. The housing 720 comprises two halves or sections 725 and 726 with a folded needle panel 742 extending therebetween. As depicted, the needle panel 742 includes three segments 743a-743c, although the panel can include any suitable number of segments, including a single segment. The two sections 725 and 726 can be disengaged from each other but preferably remain attached to the needle panel 742. When the panel 742 is folded into three segments, the panel is connected to opposite longitudinal edges of the housing sections 725 and 726. Each surface (i.e., front and rear) of the needle panel 742 can include an adhesive layer 744 (such as an adhesive paper layer), for securing needles 12 and their associated sutures 14 thereto. As shown, the sutures 14 can be attached to the adhesive layer 744 in a generally serpentine pattern, in a generally spiral pattern (where the suture extends from the needle and terminates in a spiral pattern on the adhesive layer 744), or in any other suitable pattern. Each section can include a single needle 12 and suture 14 adhered on each side thereof, as shown. Alternatively, each section can include a plurality of needles and sutures adhered on each side.

A pair of cords 746a and 746b can extend through openings in the needle panel 742 and through at least one housing section, such as housing section 726, and be used to extend and collapse the panel into the housing. Optionally, the panel cords 746a and 746b can further extend through the first housing section 725. The apparatus 710 can include one or more silicone or foam blocks 771 (or walls or sheets) secured to the inner surface(s) of the housing sections 725 and 726. Two such foam blocks 771a and 771 b are shown in FIGS. 36 and 37, one within each of the housing sections 725 and 726 to which used needles 12' can be secured (or "tacked") thereto. Preferably, the blocks 771 are positioned within the housing so as to not interfere with the expansion and collapsion of the panel 742.

Optionally, the housing 710 can include a lock. For example, a male member 780 can be located on one section of the housing and a cooperating female member 782 can be located on the other section for locking the two sections of the housing together thereby providing a clasp. To open the housing 120, a practitioner manipulates a pair of suitable instruments to apply gentle force on each section 725, 726 of the housing to open the clasp and disengage the two sections. Alternatively, a portion of each section can be magnetized so as to provide a magnetic lock. Other suitable locking mechanisms can be employed as well. For example, the cords 746a and 746b can include slidable stoppers 790a and 790b that slide along the cords and when slid against the outer surface of the housing when the housing is in the closed configuration, lock the housing closed.

Figure 38:
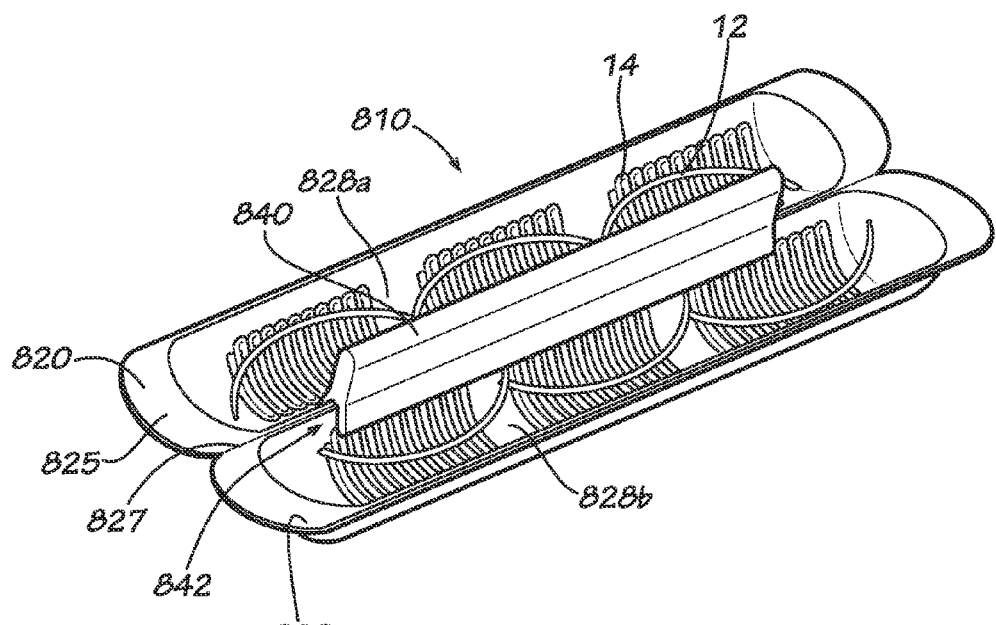
FIG. 38 is a front perspective view of an apparatus for housing a plurality of needles according to another example embodiment and shown in an open configuration.
Figure 39:
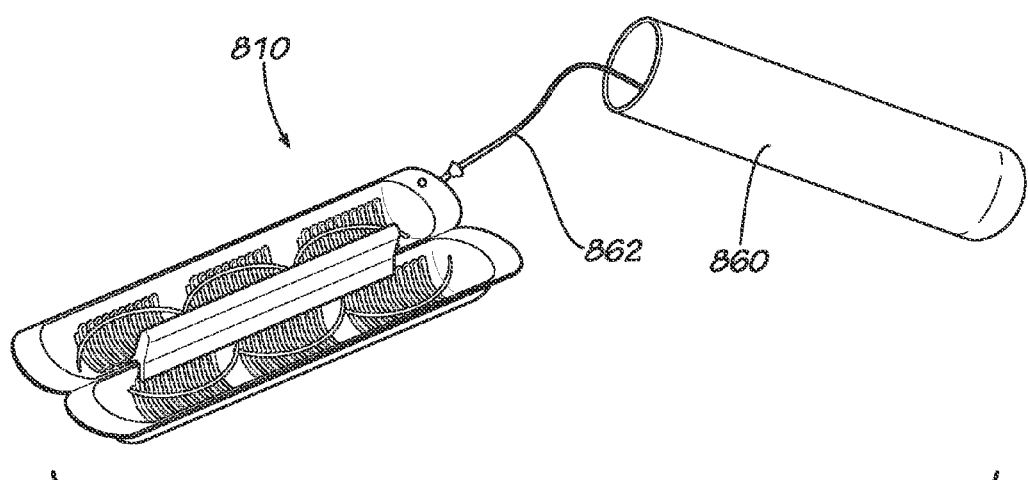
FIG. 39 is a front perspective view of the apparatus of FIG. 38 and shown tethered to a cap.
Figure 40:
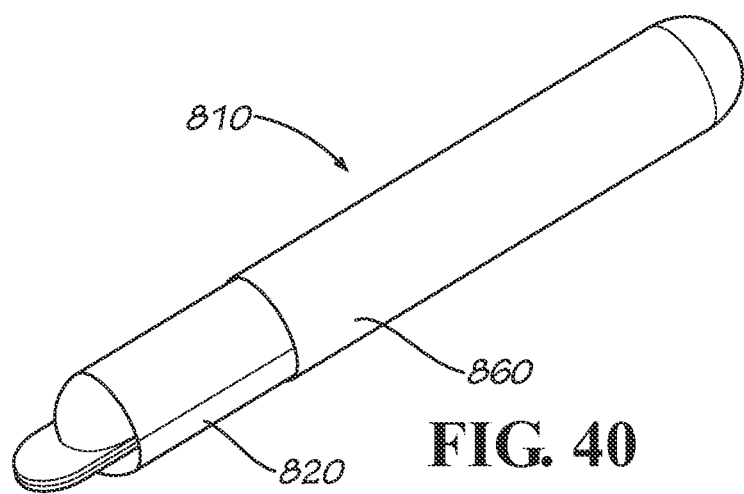
FIG. 40 is a front perspective view of the apparatus of FIGS. 38 and 39 and shown in a closed configuration with the cap thereon.

FIGS. 38-40 depict an apparatus 810 for housing a plurality of needles 12, each having an associated suture 14, according to another example embodiment. The apparatus 810 is substantially similar to the apparatus 10, but with the exceptions noted herein. The apparatus 810 comprises a housing 820 comprising two housing sections 825 and 826 hingedly attached along longitudinal edges 827 thereof. The inner surfaces of the housing sections 825 and 826 each preferably include an adhesive layer 828a, 828b (respectively) for attaching needles 12 and their associated sutures 14 thereto. Three needles with associated sutures are shown adhered in each section of the housing, although each section can accommodate fewer or additional needles and sutures. As shown, the sutures 14 can be attached to the adhesive layer in a generally serpentine pattern. Alternatively, the sutures can be attached to the adhesive layer in a generally spiral pattern or in any other suitable pattern. Preferably, a needle disposal block 840 or sheet extends from the hinged sides of the section of the housing. The needle disposal block 840 can comprise a soft and flexible (or somewhat flexible) material. Preferably, the block 840 is formed of a sheet of silicone material or other polymeric material into which used needles can be tacked. The needle disposal block 840 includes a generally Y-shaped attachment flange 842, wherein a first section of the Y portion is attached to the first housing section 825 and a second section of the Y portion is attached to the second housing section 826. Thus, the needle disposal block 840 does not interfere with the opening or closing of the housing 820. Accordingly, a used needle 12' can be tacked into the block 840 after use. Alternatively or additionally, the used needles can be secured on the same adhesive layer that secures the sterile needles 12.

As seen in FIGS. 39 and 40, the apparatus 810 can further comprise a sleeve or elongated end cap 860. Preferably, the cap 860 is connected to the housing 820 with a tether cord 862. The elongated cap 860 is generally the same shape as and slightly larger in diameter than the housing 820. The elongated cap can be flexible or it can be substantially rigid. The cap 860 includes an opening at an end thereof for receiving at least a portion of the housing 820 therethrough. The tether cord 862 is a cord of suitable length used to tether the housing 820 and the elongated cap 860 together. FIG. 40 shows the apparatus 810 with the elongated cap 860 slid over the housing 820. Additionally, the elongated cap 860 can provide a bin for the storage of waste suture strands and/or needles.

Optionally, the housing 810 can include a suitable lock. For example, the lock can be a single clasp secured to one section of the housing that is operable to engage the second section of the housing. Alternatively, a portion of each section can be magnetized such to provide a magnetic lock.

Figure 41:
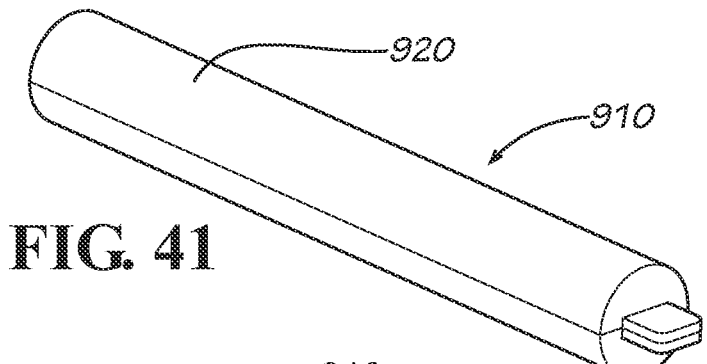
FIG. 41 is a perspective view of an apparatus for housing a plurality of needles according to another example embodiment and shown in a closed configuration.
Figure 42:
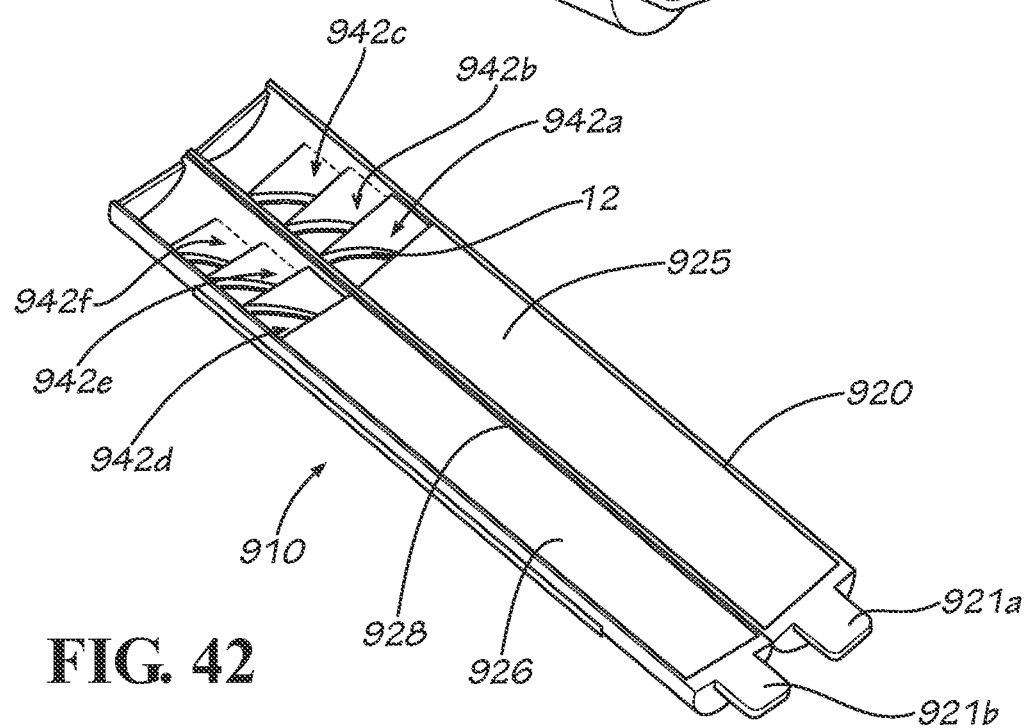
FIG. 42 is a perspective view of the apparatus of FIG. 41 and shown in an open configuration.

FIGS. 41-42 depict an apparatus 910 for housing a plurality of needles 12, each having an associated suture 14, according to another example embodiment. The apparatus 910 comprises an elongated, substantially rigid, and generally cylindrical housing 920 having first and second housing sections 925 and 226. A hinge 928 extends along adjacent longitudinal edges of the housing sections. Preferably, the housing 920 is a clamshell-type housing such that once opened, the housing 920 comprises two sections 925 and 926 hingedly connected together. The sections 925 and 926 comprise end tabs or flanges 921a, 921b attached thereto at one end thereof to provide a gripping surface for the surgical instrument. Additionally, the flanges 921a and 921b can also comprise a locking mechanism, such as a mechanical or magnetic lock for locking the apparatus 910 in its closed configuration.

Both sections comprise a plurality of needle holders 941 therein in the form of longitudinally staggered overlapping panels 930 of different lengths that form pockets for retaining the needles and sutures therein. In other words, each section includes a plurality of pockets, one for each needle and associated suture. Three such pockets 941a-941c are included in the first housing section 925, and three pockets 941d-941f are included in the second housing section 926, although the housing sections can include any suitable number of pockets. Alternatively, all needles can be housed within a single portion of the housing. The panels 930 forming the pockets can be substantially flexible, or the panels can be substantially rigid.

An instrument can be used to remove a needle 12 from a needle pocket 941 within the housing 920. After use, the used needle 12' can be inserted back into its respective pocket.

Figure 43:
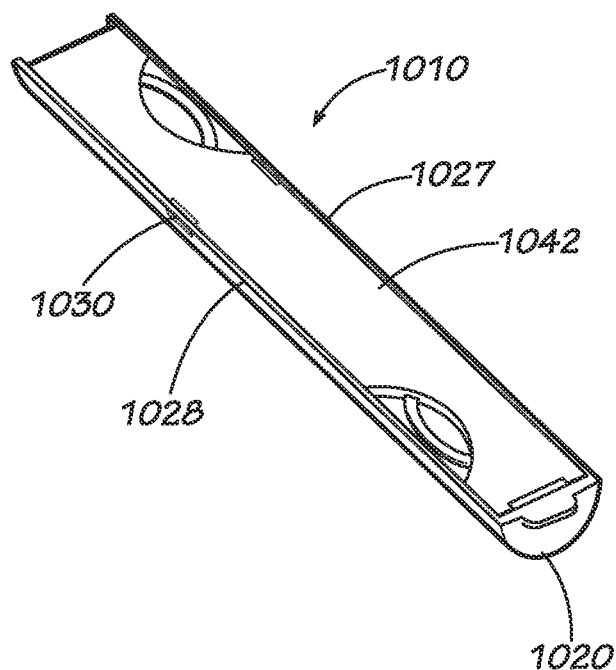
FIG. 43 is a perspective view of an apparatus for housing a plurality of needles according to another example embodiment and shown in a closed configuration.
Figure 44:
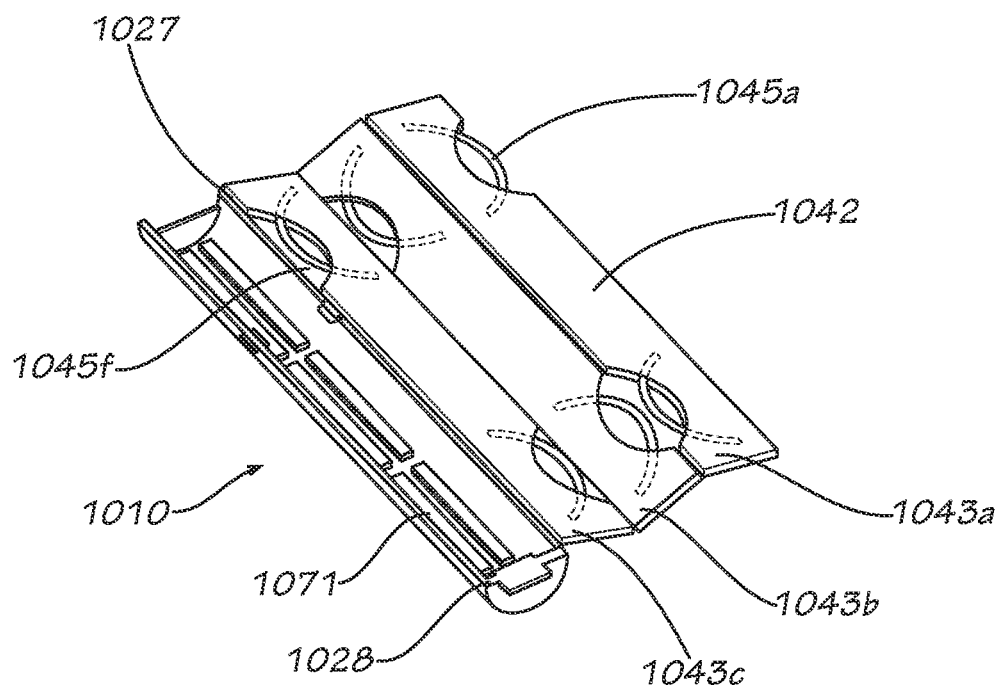
FIG. 44 is a perspective view of the apparatus of FIG. 43 and shown in an open configuration.

FIGS. 43-44 depict an apparatus 1010 for housing a plurality of needles 12, each having an associated suture, according to another example embodiment. The apparatus 1010 has a generally semi-cylindrically shaped housing 1020. In an alternative embodiment, the housing can include a second semi-cylindrically shaped member hingedly connected thereto or a substantially flat panel member hingedly attached thereto. In such embodiment, the second member can function as a lid and/or comprise a used needle retaining chamber as discussed herein. Referring to FIG. 43, the apparatus 1010 includes a needle holder 1042 in the form of a folding panel, attached to a longitudinal edge 1027 of the housing 1020. The opposite longitudinal edge 1028 can include a clasp or latch 1030 for retaining the panel in a closed configuration. The folding panel 1042 preferably comprises a substantially rigid material, although in alternative embodiments, the material can be substantially non-rigid or flexible. Also preferably, the panel 1042 is folded into three segments 1043a-1043c, each segment housing a pair of needles, although in an alternative embodiment, the panel can be folded into fewer or additional segments. As depicted, a needle 12 is positioned within a semi-circular recess 1045 (e.g., a cutout) at a longitudinal edge of the segment. The cutouts 1045a-1045f can be positioned at any suitable location along the edge of or within each segment and can be any suitable shape. In the depicted embodiment, each segment includes a cutout on each longitudinal edge at opposing ends, with the panels made of two plies to form pockets adjacent the cutouts for receiving the needles 12. The folding panel 1042 can be unfolded, as shown in FIG. 44. Once the panel 1042 is unfolded, a user can extract the needles 12 and their associated sutures 14 from the cutout 1045 using an appropriate instrument I by gripping the needle 12 and removing the needle from the folding panel 1042. The apparatus 1010 can also include at least one but preferably a plurality of foam disposal strips 1071 attached to an inner surface of the housing 1020. Used needles 12' can be "tacked" onto the strips 1071 for disposal. Alternatively, an adhesive layer can be secured to an inner surface of the housing such that the needles can be secured thereto. Also preferably, a flange 1050 extends from at least one longitudinal end of the housing 1020 to provide a gripping surface for the surgical instrument.

Figure 45:
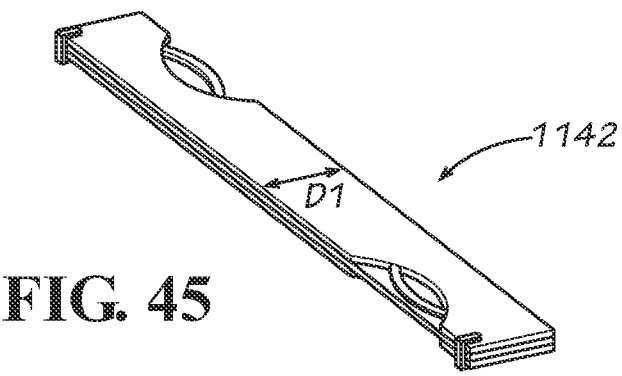
FIG. 45 is a perspective view of an apparatus for housing a plurality of needles according to another example embodiment and shown in a closed configuration.
Figure 46:
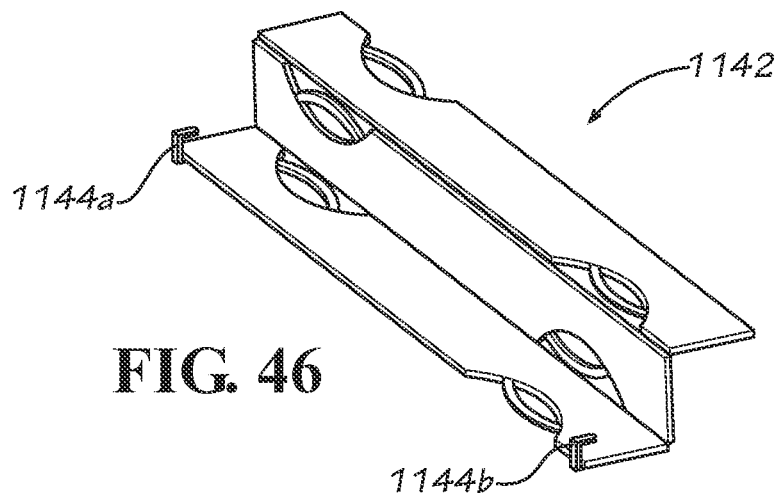
FIG. 46 is a perspective view of the apparatus of FIG. 45 and shown in a partially open configuration.
Figure 47:
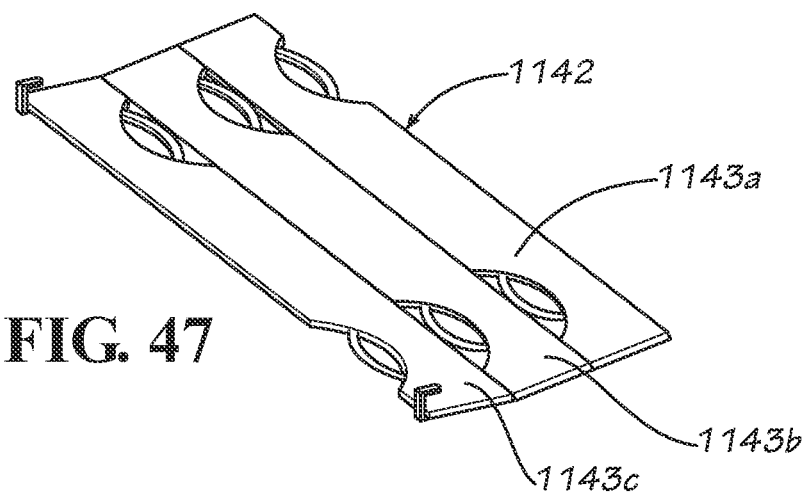
FIG. 47 is a perspective view of the apparatus of FIG. 45 and shown in a substantially fully open configuration.
Figure 48:
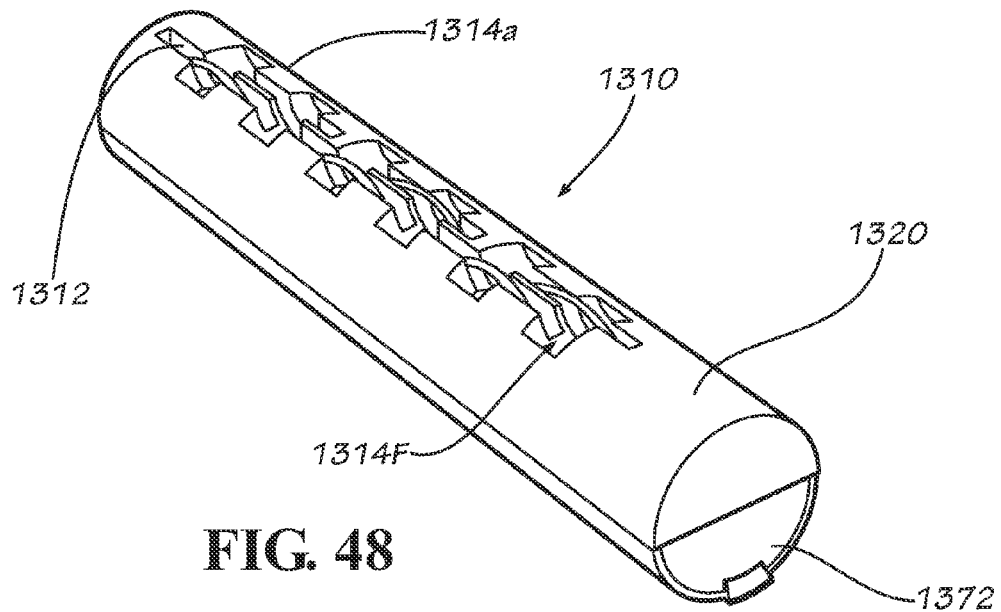
FIG. 48 is a perspective view of an apparatus for housing a plurality of needles according to another example embodiment.
Figure 49:
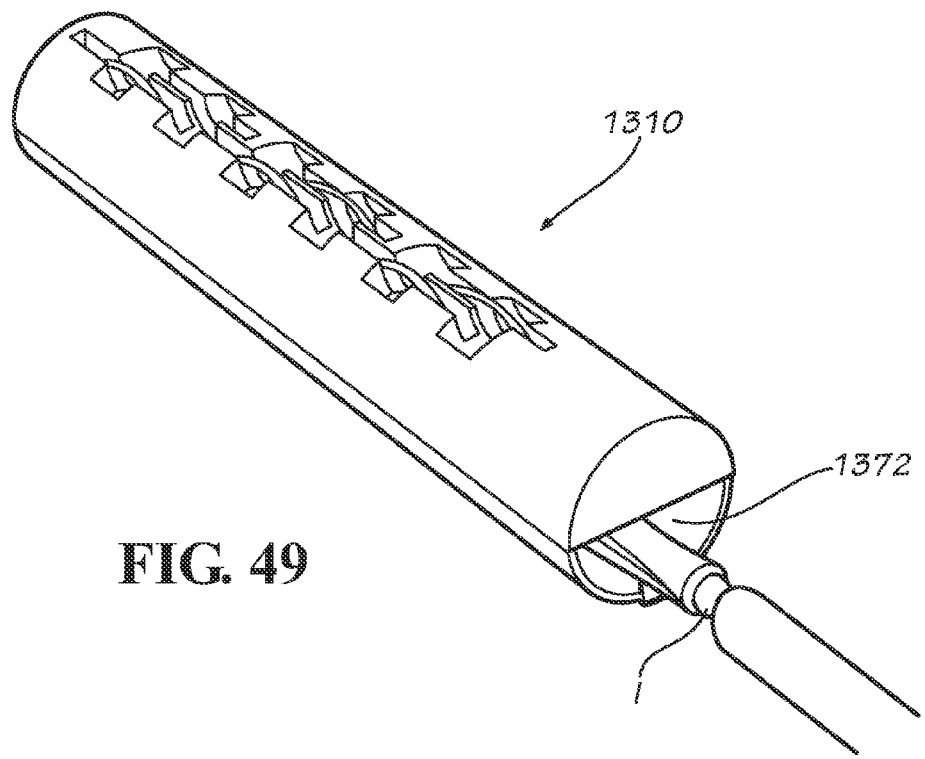
FIG. 49 is a perspective view of the apparatus of FIG. 48 and show an instrument engaging a door to a needle disposal chamber.
Figure 50:
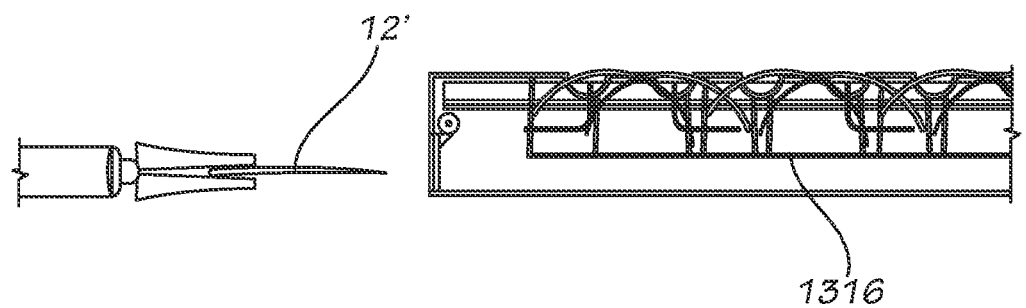
FIGS. 50-52 show side sectional views of the apparatus of FIG. 48.
Figure 51:
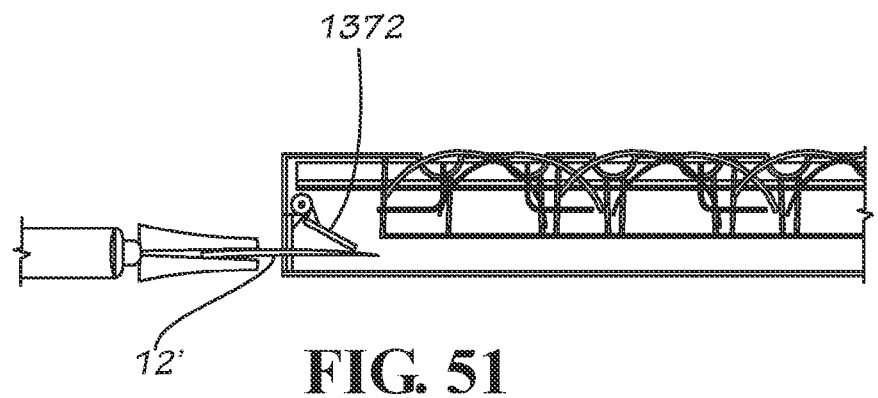
Figure 52:
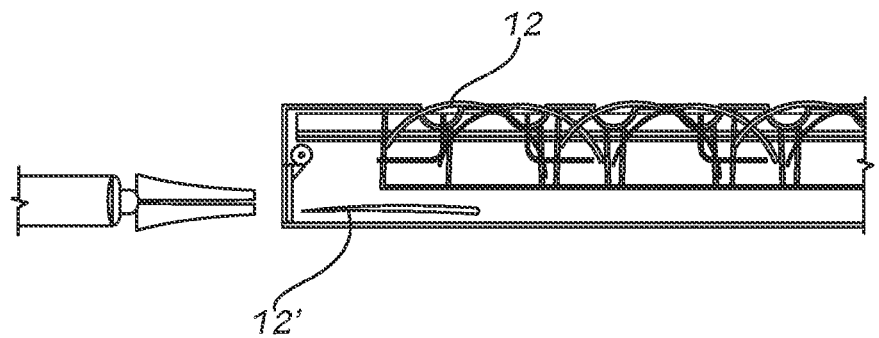

FIGS. 45-47 depict a folding panel 1142 according to another example embodiment. The folding panel 1142 is substantially similar to the panel 1042, but with the exceptions noted herein. As shown, the apparatus has a largest cross-sectional dimension D1. The dimension D1 is preferably less than about 12 mm, although this dimension can be larger as desired. The folding panel 1142 includes three segments 1143a-1143c and is initially in a compact configuration held together by a pair of panel clips 1144a and 1144b extending from one end of the panel. The panel clips 1144 are hook-like protrusions attached to one lateral free edge of a panel section on opposing ends. The folding panel 1142 is held in a compact configuration by the panel clips 1144 until the panel sections are disengaged from the panel clips 1144, allowing the folding panel 1142 to be unfolded. In one embodiment, the folding panel 1142 can be used as shown (without a suitable housing). In another embodiment, the panel can be housed within a suitable housing. Six cutouts 1145a-1145f are shown, one for each needle, although the panel 1142 can include any suitable number of cutouts positioned at any suitable place along the panel segments.

FIGS. 48-52 depict an apparatus 1310 for holding a plurality of needles 12, each having an associated suture 14, according to another example embodiment. The apparatus 1310 comprises a housing 1320, which is generally elongated and cylindrically shaped and is preferably constructed of a substantially rigid material. A longitudinal opening or channel 1312 having a plurality of laterally extending openings 1314a-1314f (or tooth-shaped openings) is located along one portion of the housing 1320. A plurality of needles 12 is housed in a generally linear arrangement within the longitudinal opening. For example, the needles can be secured to a foam strip 1316 in the housing, or they can be secured, for example, with one or more suitable clips (not shown). The laterally extending openings 1314a-1314f are generally "tooth-shaped" so as to allow a suitable instrument I to enter the opening and grasp and extract a needle 12. As shown, the apparatus comprises generally two rows of needles within the longitudinal opening or channel 1312. The needles are preferably housed within the housing and accessed via the longitudinal opening to preserve their sterility. Additionally, the housing 1320 can comprise an enclosed disposal chamber 1370 therein for receiving used needles 12'. The disposal chamber 1370 can be accessed via a chamber door 1372 located at a longitudinal end of the housing. Preferably, the chamber door 1372 is a spring-biased flap (similar to the door 74 of FIG. 1) that can be depressed by an instrument I to access the chamber 1370, as shown more clearly in FIGS. 49 and 52.

Figure 53:
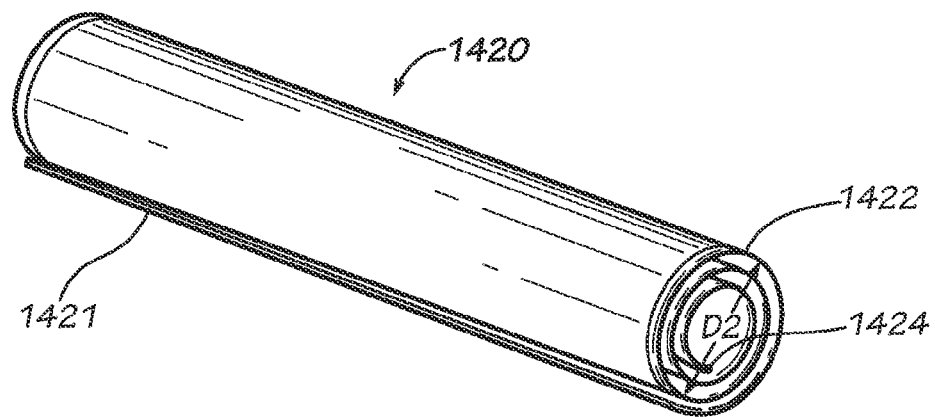
FIG. 53 is a perspective view of an apparatus for housing a plurality of needles according to another example embodiment and shown in a closed configuration.
Figure 54:
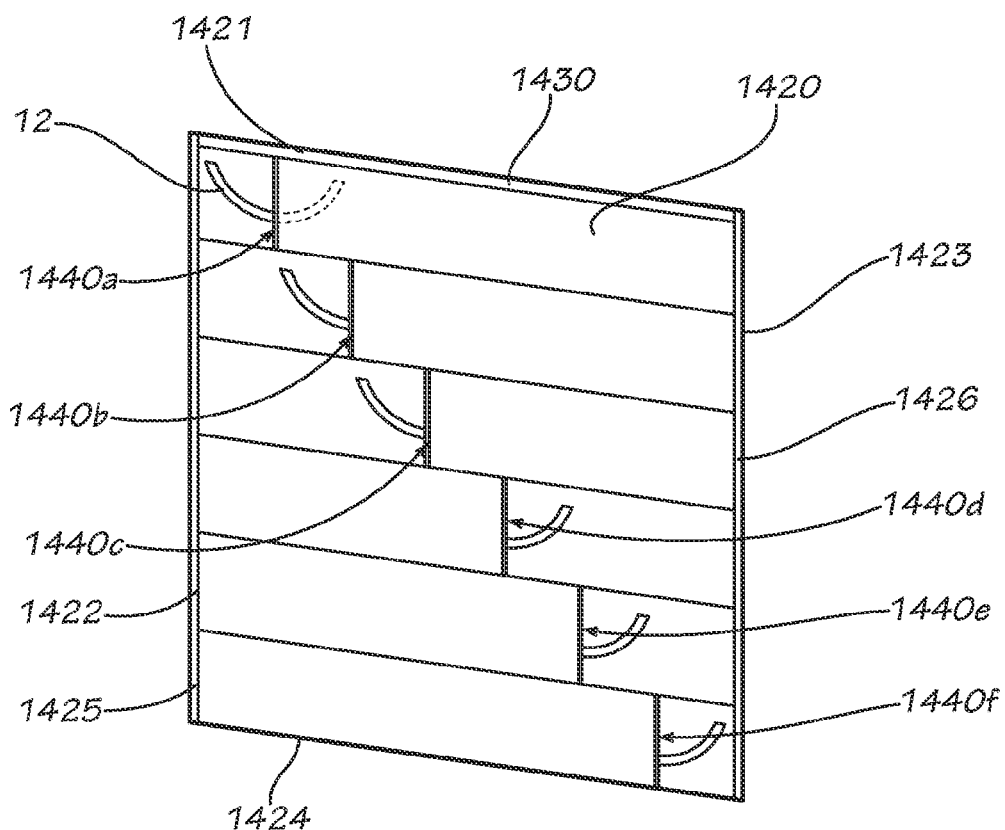
FIG. 54 is a perspective view of the apparatus of FIG. 53 in an open configuration.

FIGS. 53 and 54 depict a flexible panel 1420 for holding a plurality of needles 12, each having an associated suture 14, according to another example embodiment. In the closed or rolled-up configuration, the panel 1420 has dimensions of about 6 cm long and about 11 mm in diameter (or cross-sectional dimension D2), although the dimensions can vary as desired. In the open, or unfolded configuration, the panel 1420 has dimensions of about 6 cm by about 6 cm. These dimensions are exemplary for the depicted embodiment, and can be larger or smaller, as desired. The flexible panel 1420 preferably comprises a flexible, nontearable polymeric material. In alternative embodiments, other suitable materials, such as thin metals or other fabrics, can be employed.

The flexible panel includes an upper edge 1421, first and second opposing, longitudinal edges 1422 and 1423, and a lower edge 1424. The panel 1420 can further comprise wire strips 1425 and 1426, one along each longitudinal edge, secured thereto. In a typical commercial embodiment, the strips 1425 and 1426 are nitinol strips. For example, the wire strips 1425 and 1426 can be curved resilient wires. The strips 1425 and 1426 aid in rolling up the panel 1420 and securing the panel in a rolled-up or closed configuration. Thus, the panel 1420 can be manipulated by a tool to force it to open flat (in the "open" configuration) for use, and when the panel is released, it tends to return to a generally cylindrical closed position or state due to resilient curved wires. The flexible panel 1420 can optionally be stored within a suitable cylindrically-shaped housing (such as a tube with at least one open end) in a rolled-up or "closed" configuration.

Alternatively or additionally, the panel 1420 can include an adhesive strip 1430 along one longitudinal edge, such as the upper edge 1421 thereof, for retaining the panel in a closed configuration. The flexible panel 1420 can be unrolled, as shown in FIG. 54, exposing a plurality of needle and suture holders 1440 in the form of needle pockets. Six needle pockets 1440a-1440f are shown, although the flexible panel 1420 can include any suitable number of pockets. In the depicted embodiment, the needle pockets 1440a-1440f are arranged such that the lip of each pocket is horizontally/laterally offset from one another in a staggered or stepped arrangement, with three of the pockets 1440a-1440c opening towards the first longitudinal edge 1422 and the other three pockets 1440d-1440e opening towards the opposite longitudinal edge 1423, although any suitable arrangement can be used. The staggered arrangement provides for reduced overlapping of the needles so that the overall diameter of the rolled-up assembly is minimized. The panel 1420 can be rolled up into the closed configuration with the top edge 1421 being on the outside of the generally cylindrical structure. The pockets can be shallow enough that the needles are not completely received in them (i.e., portions of the needles are exposed) as depicted, or they can be deep enough to completely receive the needles.

Figure 55:
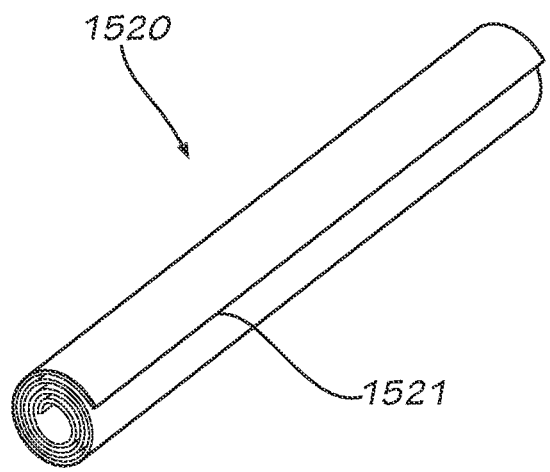
FIG. 55 is a perspective view of an apparatus for housing a plurality of needles according to another example embodiment and shown in a closed configuration.
Figure 56:
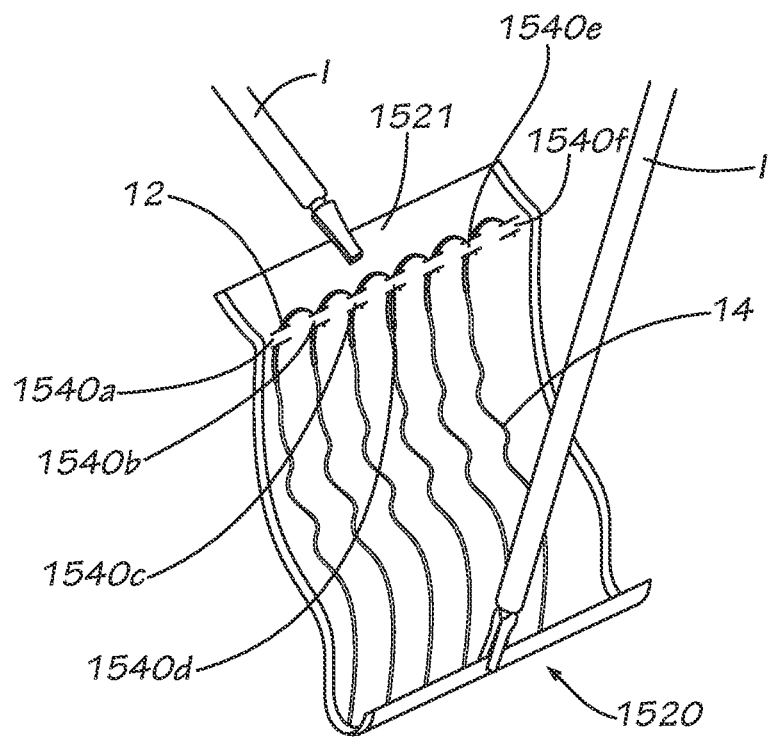
FIG. 56 is a perspective view of the apparatus of FIG. 55 in an open configuration.
Figure 57:
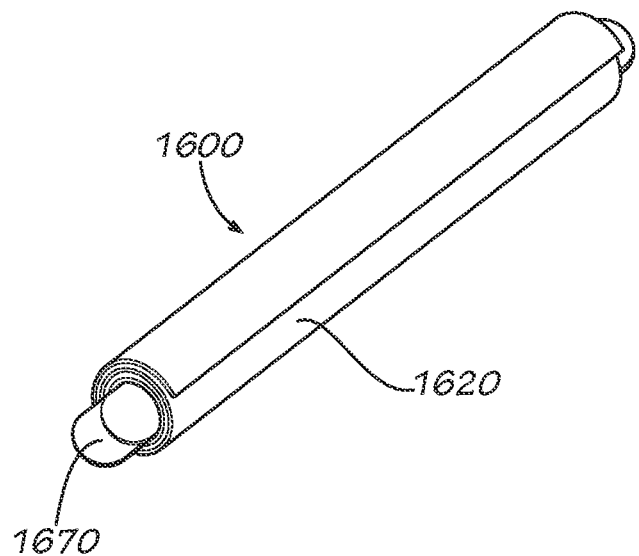
FIG. 57 is a perspective view of an apparatus for housing a plurality of needles according to another example embodiment and shown in a closed configuration.
Figure 58:
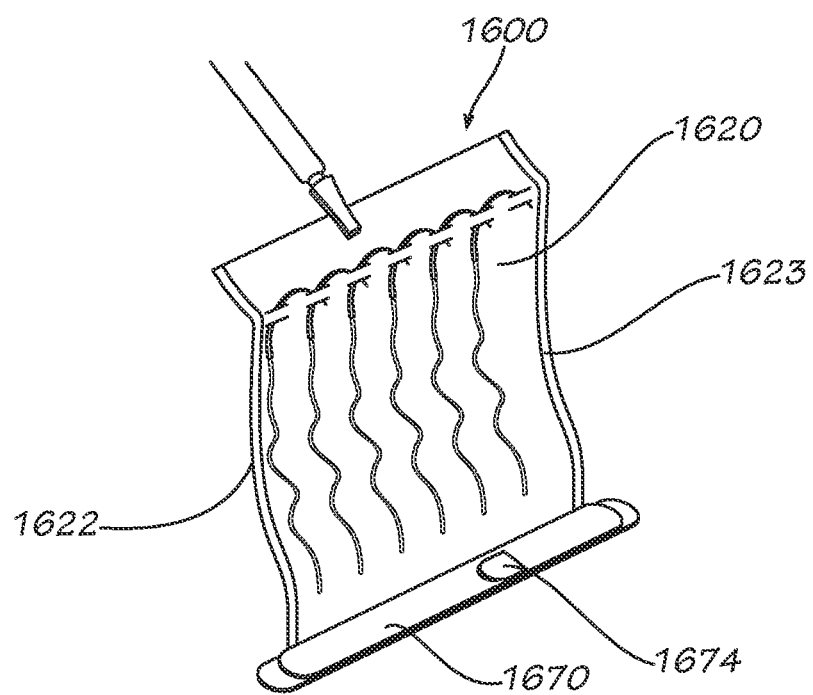
FIG. 58 is a perspective view of the apparatus of FIG. 57 in an open configuration.

FIGS. 55 and 56 depict perspective views of an apparatus or flexible panel 1520 for housing a plurality of needles 12 and sutures 14 according to another example embodiment.

The flexible panel 1520 is substantially similar to the flexible panel 1420 but with the exceptions noted herein. The flexible panel 1520, like flexible panel 1420, has a diameter of 11 mm when rolled up in its closed configuration, but this diameter can be larger or smaller as desired.

In the depicted embodiment, the needle pockets 1540 are arranged in line near the top edge 1521 of the panel, although any suitable arrangement can be used. Six needle 1540a-1540f pockets are shown, although the panel can include any suitable number of needle pockets. Alternatively, a plurality of straps and/or adhesive can be used to secure the needles 12 and corresponding sutures 14 to the panel. Additionally, preferably, the panel 1520 is rolled up into the closed configuration with the top edge 1521 being on the outside of the generally cylindrical structure. As shown in FIG. 56, two suitable instruments I can be used to unroll and manipulate the panel.

FIGS. 57-60 depict various perspective views of an apparatus 1600 for housing a plurality of needles 12 and sutures 14 according to another example embodiment. The apparatus 1600 is substantially similar to the apparatus 1500 but with the exceptions noted herein. The apparatus 1600 includes a flexible panel 1620 having an enclosed needle disposal device 1670 permanently or semi-permanently attached to the base of the panel. Alternatively, the flexible panel 1620 can be releasably secured to the disposal device 1670. In a closed position, the flexible panel 1620 wraps around the disposal device 1670 and is held in place with the lateral wire strips 1622 and 1623. When the flexible panel 1620 is wrapped around the disposal device 1670 in its closed configuration, the apparatus has a diameter of less than about 12 mm, but this diameter can be larger or smaller as desired. In a typical embodiment, the diameter is about 11 mm. Optionally, an adhesive or other fastener or fastening technique can be used to secure the panel 1620 in a closed position such as by applying an adhesive strip to an upper edge of the panel.

The disposal device 1670 can be constructed of a rigid or substantially rigid material (such as a plastic). The disposal device 1670 can be substantially similar to the disposal chamber 70 depicted in FIGS. 1 and 2. The disposal device 1670 has a generally enclosed semi-cylindrical housing having a door 1674 or hatch in a wall thereof that provides access thereto. Preferably, the door is a pressure-sensitive flap that can be depressed to access the chamber 1670. In other words, the door can be spring-biased such that it is held in the closed position until sufficient force is exerted thereon to open the door. A used needle can be placed inside the chamber and securely held therein. Although the disposal device 1670 is shown as generally semi-cylindrical, any suitably sized and shaped disposal device can be employed.

Figure 59:
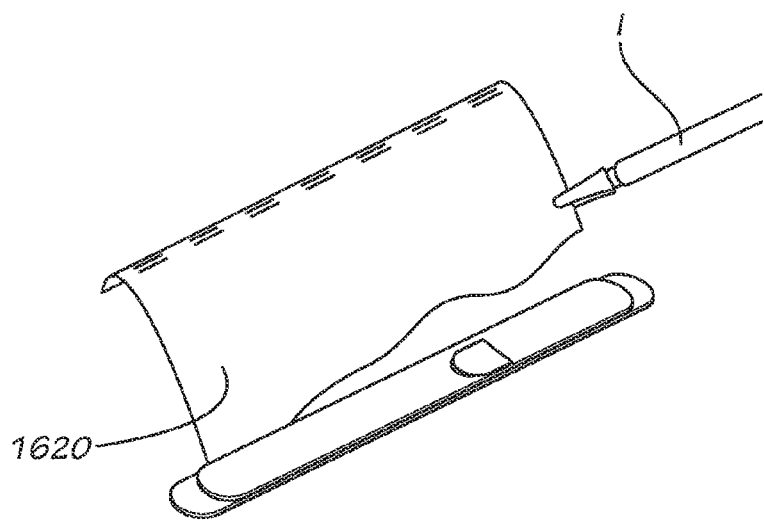
FIG. 59 is a perspective view of the apparatus of FIG. 57 and shown with a panel portion thereof partially detached from a disposal portion.
Figure 60:
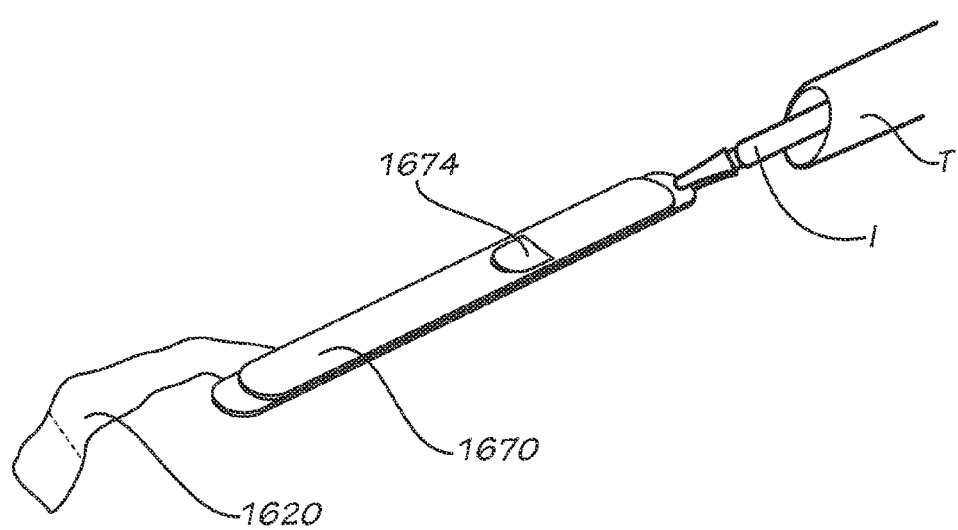
FIG. 60 is a perspective view of the apparatus of FIG. 57 and shown in a configuration suitable for removal through a trocar.

Optionally, after use, the flexible panel 1620 can be at least partially detached (or fully detached) from the disposal chamber 1670 (such as by cutting the panel with an appropriate instrument), as shown in FIGS. 59 and 60, so as to aid in the removal of the device 1600 from the subject through a trocar T inserted through a surgical port in the body of the subject. Alternatively, after use, the panel can be wrapped around the disposal chamber and configured in the closed configuration, and then removed from the subject through a surgical port. Still alternatively, any of the disposal devices/chambers of the present invention can be used with the panel 1620.

In an alternative embodiment, the panel 1420 of FIGS. 53 and 54 can be attached to a disposal device, such as the disposal device 1670 or any other disposal device of the present invention.

FIGS. 61-66 depict various views of an apparatus 1700 for housing a plurality of needles 12 according to another example embodiment. The apparatus 1700 is substantially similar to the apparatus 10 and 110 of previously described embodiments, but with the exceptions noted herein. Thus, in this embodiment as in previous embodiments, the apparatus 1700 includes a housing 1720 with first and second sections 1725 and 1726, a first needle holder (not shown) for unused needles (e.g., threaded with sutures) located in the first section, and a second needle holder for used needles 12' located in the second section. The first needle holder is typically provided by at least one (e.g., two) block of a tackable material. And the second needle holder is typically provided by a substantially enclosed chamber 1770 formed by the second outer wall 1726 and an internal divider wall 1778 (with an access door/hatch).

In this embodiment, however, the outer wall 1726 (or a portion thereof) of the housing 1720 is constructed of a substantially transparent or semi-transparent material such as a clear plastic. Thus, for example, when using a 3D HD visualization (i.e., the magnification and resolution afforded by the robotic technology), the practitioner can see (through the wall 1726) and count the number of used needles 12' stored in the enclosed chamber 1770. In some embodiments, such as those in which the unused needles (held by the first needle holder) are not visible when the housing is in the opened position, the other wall 1725 (or a portion thereof) of the housing 1720 is also constructed of a substantially transparent or semi-transparent material for seeing and counting the numbers of unused needles in the housing. But in the depicted embodiment, that is not needed because the unused needles can be seen and counted when the housing 1720 is in the open position. In addition, this transparent-outer-wall feature can be included in other embodiments in which the first and second needle holders are provided in other forms.

Accordingly, because the outer wall 1726 of the housing 1720 is substantially transparent or semi-transparent, even after the housing is closed, the surgeon is able to see (through the wall) and count the used needles 12' contained in the housing chamber 1770 (effectively, a "sharps container") before removing the apparatus 1700 from the patient's body (e.g., the peritoneal or thoracic cavity). And in the depicted embodiment, the unused needles are visible when the housing 1720 is in the opened position, so the surgeon can see and count them before closing the housing. In particular, using robotic technology, the surgeon can view a 3D HD image of the apparatus 1700, which makes needle counting quick and easy. At the same time, the nurses in the room can quickly and easily count the needles by looking at the 2D (or 3D) monitors in the operating room. If the apparatus 1700 is removed immediately after such a needle count, the operating-room staff may be able to avoid the step of opening the sharps chamber 1770 to physically count each used needle 12' again. In this way, the operating room staff can quickly and easily confirm that the number of needles in the housing 1720 when it is removed from the patient's body is the same as when it was inserted, thereby ensuring that no needles are accidentally left in the patient's body. And if desired the staff can still physically count the needles after the apparatus is removed from the body by opening the sharps chamber 1770 (e.g., by sliding, pivoting, or at least partially removing the divider wall 1778 or a door thereof) and removing them from the opened sharps chamber.

In addition, the apparatus 1700 includes at least one tab cord 1723 for facilitating the removal of the apparatus from the patient's body through the trocar. In the depicted embodiment, the tab cord 1723 is provided by a length of a flexible biocompatible material such as a plastic. The depicted cord 1723 can be inserted through a first aperture 1721 in a tab extending from one of the ends of the housing 1720 (or through a first set of aligned apertures in two housing tabs that are adjacent each other when the housing is closed). In the depicted embodiment, the tab cord 1723 is formed into a closed loop with its free end portions 1724 coupled together (e.g., by tying or a connector).

In embodiments in which the looped cord 1723 is routed through a set of aligned apertures in the housing tabs, the effective length of the looped cord when pulled tight (i.e., about one-half the actual length of the cord when not looped) can be selected so that it limits the housing sections 1725 and 1726 from pivoting open farther than their intended opened angle (which is typically about 180°). In some embodiments, a second tab cord (not shown) is included at the opposite end of the housing, the tab cord is not in a closed loop (i.e., not doubled over and its free ends not adjacent each other), and/or the tab cord includes stoppers (e.g., one or more conical, spherical, and/or other-shaped elements) near the free ends thereof that retain the cord and prevent it from sliding through the apertures. In embodiments including stoppers on the tab cord, the length of the cord and the position of the stoppers on the cord can be selected to limit the housing sections from pivoting open farther than their intended opened angle.

Advantageously, the tab cord 1723 can be grasped and pulled to remove the apparatus 1700 from the body of the human or animal subject. In particular, the tab cord 1723 can be grasped and pulled by the instrument I, which is inserted through the trocar and controlled by the surgeon or surgical assistant, to pull the apparatus 1700 out of the body through the trocar. Because the cord is flexible, when the apparatus 1700 is pulled by the tab cord 1723 and the curved end of the housing 1720 contacts the trocar, the apparatus orients itself into alignment with the trocar lumen for removal through it. This can be helpful, for example, in cases where the surgical assistant removes the apparatus 170 using traditional "straight stick" laparoscopic instruments and 2D monitors. In such cases, it is easier to grasp the tab cord 1723 and pull the apparatus 1700 through the trocar than to grasp the integral tabs of the housing 1720 directly.

In addition, the depicted apparatus 1700 has a modified locking mechanism (for a snap-fit closure means that provides ease of opening using the instrument I) as well as gripping ridges on the tabs of both ends of the housing 1720 (for grasping by the instrument I). Furthermore, the housing tabs 1750 are modified in that the tabs on one side of the housing 1720 do not extend the full width of the housing, so that the aperture for the pull tab 1723 is only formed on the other tab that does extend the full width of the housing.

Figure 67:
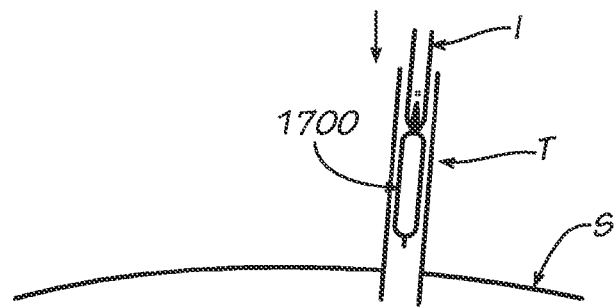
FIGS. 67-69 are side views of the apparatus of FIGS. 61-66 shown in use during a surgical procedure.
Figure 68:
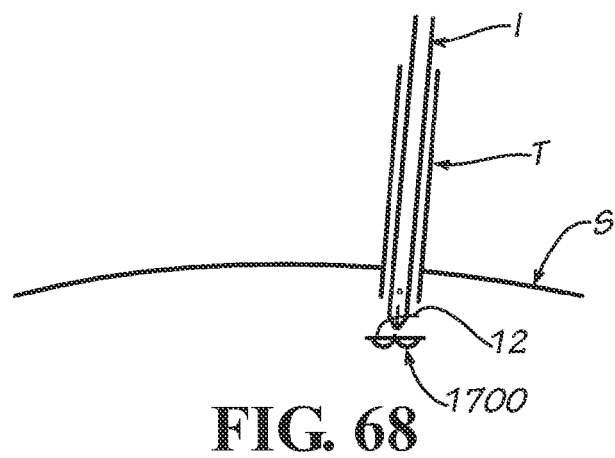
Figure 69:
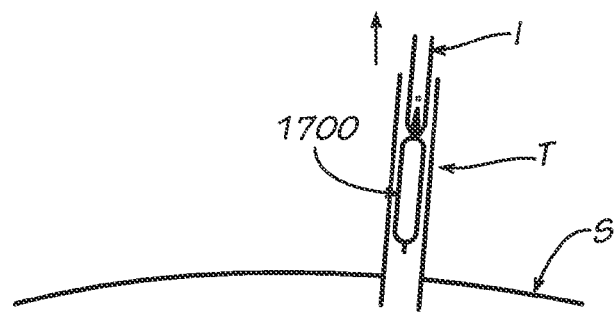

In use, any of the apparatuses of the present invention can be placed on, in, or near a human or animal subject during a robot-assisted endoscopic surgical procedure or other medical procedure utilizing sutures. Typically, the apparatus is placed inside the body of the subject. For illustration purposes, an example sacrocolpopexy procedure is depicted in FIGS. 67-69 using the appratus 1700. In the depicted procedure, the apparatus 1700, in its closed configuration, can be placed through a trocar T (or other suitable medical instrument) extending through an incision and into the subject's abdomen S. The practitioner can then use instruments I of a robotic surgical system or conventional laparoscopic instruments, with the apparatus 1700 inside the patient's body S, to grasp the housing 1720 and manipulate it into an appropriate/suitable location in the body where the practitioner can easily access the needles 12. The practitioner, using the instruments I, then opens up the housing 1720 to reveal the plurality of needles 12 with sutures. Once opened, the practitioner can grasp a needle 12, still using the robotic or conventional laparoscopic instruments I, suture the appropriate tissue of the subject, and return the used needle (and any remaining unused suture) to the disposal portion 1770 of the apparatus 1700. Upon completion of all suturing or use of all needles 12, the housing 1720 is then closed and removed from the body S through the trocar T in the incision for disposal. If additional suturing is to be done, a second apparatus can be inserted through the trocar and the steps of manipulating the housing and needles can be repeated.

Nothing herein shall be construed to limit the use of the apparatus of the present invention to use with robotic surgical equipment, except a positive recitation of such use in the claims. The apparatus can be used in any surgical or medical setting where the use of one or more sutures is desired. And the apparatus can be used without a trocar; it can be inserted into the body through a small incision without a trocar inserted into the incision.

It will be understood that any of the storage, disposal, and locking assemblies of any of the embodiments of FIGS. 1-66 can be interchangeably substituted into any other of the embodiments. In other words, any of the elements or features of some example embodiments of the present invention can be combined with other elements of other example embodiments. For example, any of the apparatuses can include a magnetic closure or lock.

While the invention has been described with reference to preferred and example embodiments, it will be understood by those skilled in the art that a variety of modifications, additions and deletions are within the scope of the invention, as defined by the following claims.

What is claimed is:

1. An apparatus for holding a plurality of surgical needles and for use in performing robotic-assisted endoscopic surgery on a subject's body, the apparatus comprising:
  a housing including a first section and second section, said sections terminating in a first and second opposing end tabs wherein, the first tab is wider than the second tab and wherein the tabs on the first and second housing are oriented in opposite positions relative to each other such that in the closed position the first tab of the first section overlaps the second tab of the second section wherein the housing is manipulable by grasping and manipulating said tabs between a closed position in which the housing encloses an interior space and an open position in which the interior space is accessible and wherein in the closed position the housing has a largest cross-sectional lateral dimension of less than about 12 mm;
  a first needle holder that is located in the first housing section and that holds a plurality of unused ones of the needles in the interior space; and
  a second needle holder that is located in the second housing section and that receives and holds a plurality of used ones of the needles in the interior space after suturing use of the needles, wherein the second needle holder is a substantially closed chamber that receives and contains the used needles, wherein the second needle holder includes an access opening through which the used needles can be inserted into the chamber and a spring-biased door movable between a closed position covering the opening and an open position for exposing the opening for used-needle insertion.

2. The apparatus of claim 1, wherein the housing is a clamshell housing having the first section hingedly connected to the second section.

3. The apparatus of claim 2, further comprising a locking mechanism adapted to secure the housing in the closed position.

4. The apparatus of claim 1, wherein the housing further comprises an internal divider wall that cooperates with the second section of the housing to form the substantially enclosed chamber.

5. The apparatus of claim 4, wherein the access opening is formed the internal divider wall.

6. The apparatus of claim 1, wherein at least a portion of the second section of the housing is constructed of a substantially transparent or semi-transparent material through which the needles in the housing can be viewed with 3D visualization equipment to permit counting the needles before removing the apparatus from the subject's body.

7. The apparatus of claim 1, wherein the first needle holder includes at least one block of a material into which the unused needles are tacked.

8. The apparatus of claim 1, further comprising a cord extending from an end of the housing, wherein the cord can be pulled to remove the apparatus through the trocar.

9. The apparatus of claim 8, wherein the housing includes at least one aperture and the cord is flexible and routed through the at least one aperture.

10. The apparatus of claim 9, wherein the cord is formed into a closed loop.

11. The apparatus of claim 1, further comprising a plurality of sutures, wherein the needles are threaded with corresponding ones of sutures.

12. A method of using the apparatus of claim 1 in performing robotic-assisted endoscopic surgery, comprising the steps of:
placing the closed apparatus inside the human or animal subject through the incision in the subject; opening the apparatus to reveal the plurality of needles;
removing a first one of the needles from the first needle holder of the first section of the housing; using the first needle to suture tissue; storing the first needle in the second needle holder of the second section of the housing;
closing the housing; and removing the closed apparatus from the subject through the incision in the subject.

13. The method of claim 12, further comprising the step of counting the needles in the housing before removing the closed apparatus from the subject, wherein the needle-counting step includes viewing the used needles in the second needle holder of the second section through a substantially transparent or semi-transparent portion of the housing.

14. The method of claim 12, wherein the step of removing the closed apparatus from the subject includes grasping and pulling a tab cord coupled to an end tab of the housing.

15. The method of claim 12, wherein the step of placing the closed apparatus inside the subject includes inserting the closed apparatus through a trocar inserted through the incision, and wherein the step of removing the closed apparatus from the subject includes removing the closed apparatus through the trocar inserted through the incision.

16. An apparatus for holding a plurality of surgical needles and for use with a trocar in performing robotic-assisted endoscopic surgery on a subject's body, the apparatus comprising:
an elongated housing including a first section and a second section, said sections terminating in a first and second opposing end tabs wherein the first tab is wider than the second tab and wherein the tabs on the first and second housing are oriented in opposite positions relative to each other such that in the closed position the first tab of the first section overlaps the second tab of the second section wherein the housing is manipulable between a closed position in which the housing sections enclose an interior space and an open position in which the interior space is accessible, wherein in the closed position the housing has a largest cross-sectional lateral dimension of less than about 12 mm;
a first needle holder that is located in the first housing section and that holds a plurality of unused ones of the needles in the interior space;
a second needle holder that is located in the second housing section and that receives and holds a plurality of used ones of the needles in the interior space after suturing use of the needles, wherein the second needle holder is a substantially enclosed chamber that receives and contains the used needles, the housing further comprises an internal divider wall that defines an access opening and a spring-biased door covering the opening, the divider wall cooperates with the second section of the housing to form the substantially enclosed chamber, the used needles can be inserted into the chamber through the access opening, the spring-biased door pivots between a closed position covering the opening and an open position pivoted into the chamber and exposing the access opening for used needle insertion, the door is spring-biased into the closed position so that the door is normally in the closed position unless a force is applied to the door, and at least a portion of second section of the housing is made of a substantially transparent or semi-transparent material through which the used needles in the enclosed chamber can be viewed to permit counting the needles before removing the apparatus from the subject's body; and
a cord extending from an end of the housing, wherein the housing includes at least one aperture and the cord is flexible, routed through the at least one aperture, and formed into a closed loop, and wherein the cord can be pulled to remove the apparatus through the trocar, wherein in use the apparatus in the closed position can be inserted into the subject's body through the trocar, the housing can be opened, the unused needles can be removed from the first needle holder of the first housing section for suturing, the used needles can be stored in the second needle holder of the second housing section after suturing, the housing can be closed, and the apparatus in the closed position can be removed from the subject's body through the trocar.

17. The apparatus of claim 16, wherein the housing is a clamshell housing having the first section hingedly connected to the second section, and further comprising a locking mechanism adapted to secure the housing in the closed position.

18. The apparatus of claim 16, wherein the first needle holder includes at least one block of a material into which the unused needles are tacked.

19. The apparatus in claim 1, wherein the door is pivotal and spring-biased into the closed position so that the door is normally in the closed position unless a force is applied to the door, wherein in the open position the door is pivoted into the chamber, and wherein the spring-biased door pivots from the normal closed position to the open position exposing the opening for used needle insertion upon a used one of the needles being pressed against the door and then pivots back to the normal closed position upon release of the used needle in the chamber so that the used needle is no longer pressed against the door.

20. The apparatus in claim 19, wherein when the door is in the normal closed position, the chamber is substantially enclosed such that there is no space through which the used needles stored therein can pass and escape the chamber.

* * * * *